US010082655B2

(12) United States Patent
Chen et al.

(10) Patent No.: US 10,082,655 B2
(45) Date of Patent: Sep. 25, 2018

(54) DIFFERENTIAL FILTERING CHROMATIC CONFOCAL MICROSCOPIC SYSTEM

(71) Applicants: Liang-Chia Chen, Taipei (TW); Jiun-Da Lin, Taipei (TW)

(72) Inventors: Liang-Chia Chen, Taipei (TW); Jiun-Da Lin, Taipei (TW)

(73) Assignee: NATIONAL TAIWAN UNIVERSITY, Taipei (TW)

(*) Notice: Subject to any disclaimer, the term of this patent is extended or adjusted under 35 U.S.C. 154(b) by 501 days.

(21) Appl. No.: 14/464,061

(22) Filed: Aug. 20, 2014

(65) Prior Publication Data

US 2015/0055215 A1 Feb. 26, 2015

(51) Int. Cl.
*G02B 21/00* (2006.01)
*G02B 21/06* (2006.01)
(Continued)

(52) U.S. Cl.
CPC ..... *G02B 21/0068* (2013.01); *G02B 21/0032* (2013.01); *G02B 21/0064* (2013.01); *G01B 9/02036* (2013.01); *G01B 9/02042* (2013.01); *G01B 9/04* (2013.01); *G01N 21/9501* (2013.01); *G01N 2223/6116* (2013.01);
(Continued)

(58) Field of Classification Search
None
See application file for complete search history.

(56) References Cited

U.S. PATENT DOCUMENTS 5,808,735 A * 9/1998 Lee ............... G01N 21/9501
250/559.42
6,690,520 B1 * 2/2004 Kusuzawa ......... A61B 5/0073
356/343
(Continued)

FOREIGN PATENT DOCUMENTS

JP WO 2012081341 A1 * 6/2012 ......... G01N 21/8806
TW 201321714 6/2013

OTHER PUBLICATIONS

Weiqian Zhao et al., "Bipolar absolute differential confocal approach to higher spatial resolution", Oct. 18, 2004, vol. 12, No. 21, Optics Express.

*Primary Examiner* — Jennifer D Carruth
*Assistant Examiner* — Ryan S Dunning
(74) *Attorney, Agent, or Firm* — WPAT, PC

(57) ABSTRACT

A differential filtering chromatic confocal microscopic system comprises a chromatic dispersion objective for receiving and axially dispersing a broadband light from a light source and projecting dispersed lights onto an object thereby forming an object light reflected therefrom; an optical modulation module for dividing the object light into a first and a second object lights; a pair of optical intensity sensing module, respectively having a spatial filter with a different pinhole diameter or a slit width from each other, for detecting the first and second object lights, thereby obtaining a plurality of first and second optical intensity signals; and a signal processor for respectively processing the plurality of first and second optical intensity signals thereby obtaining a plurality of differential rational values of optical intensity and determining a corresponding object depth associated with each differential rational value according to a relation between signal intensity ratio and object surface depth.

12 Claims, 24 Drawing Sheets

(51) Int. Cl.
    *G01B 9/02*     (2006.01)
    *G01N 21/95*    (2006.01)
    *G01B 9/04*     (2006.01)

(52) U.S. Cl.
    CPC .... *G01N 2291/2697* (2013.01); *G02B 21/006* (2013.01); *G02B 21/0016* (2013.01); *G02B 21/0072* (2013.01)

(56) References Cited

U.S. PATENT DOCUMENTS

| | | | |
|---|---|---|---|
| 2002/0171825 A1* | 11/2002 | Krantz | G01N 21/95607 356/237.1 |
| 2004/0051879 A1 | 3/2004 | Schick | |
| 2006/0012871 A1 | 1/2006 | Funk et al. | |
| 2010/0188742 A1* | 7/2010 | Chen | G02B 21/0032 359/385 |
| 2013/0277553 A1* | 10/2013 | Otani | G01N 21/8806 250/307 |

* cited by examiner

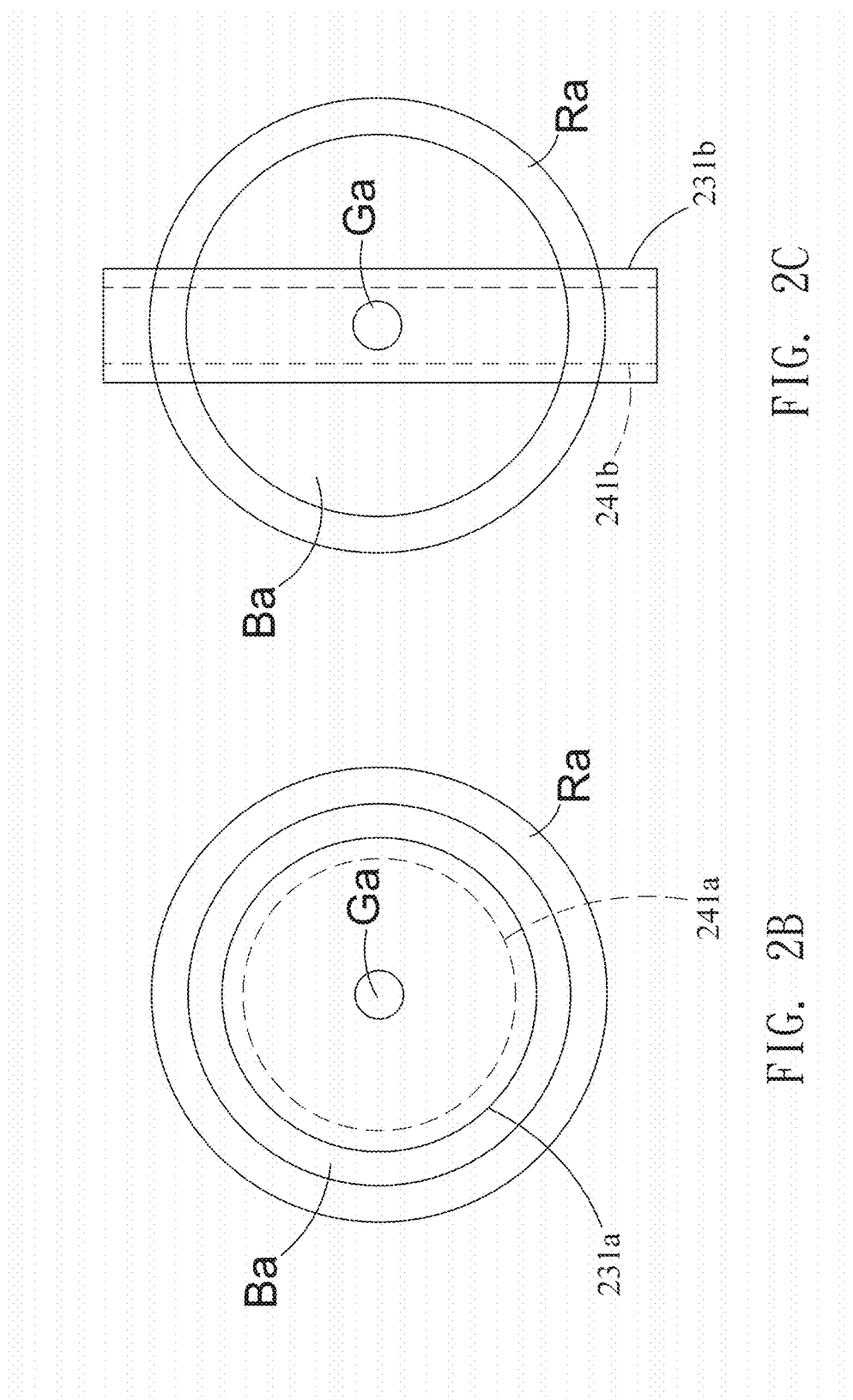

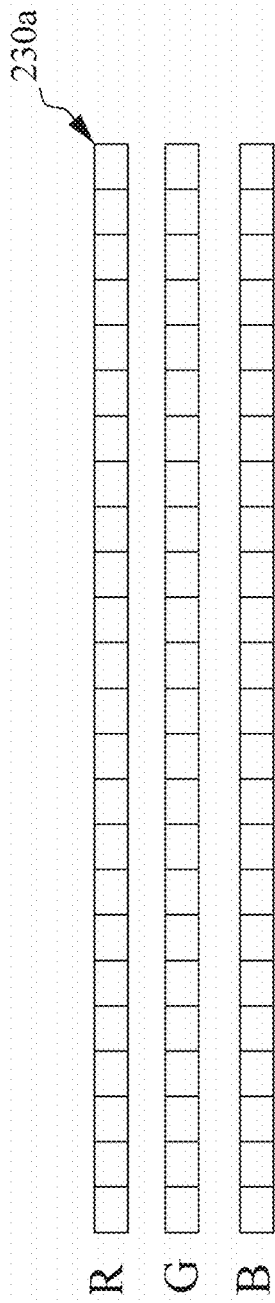
FIG. 2F
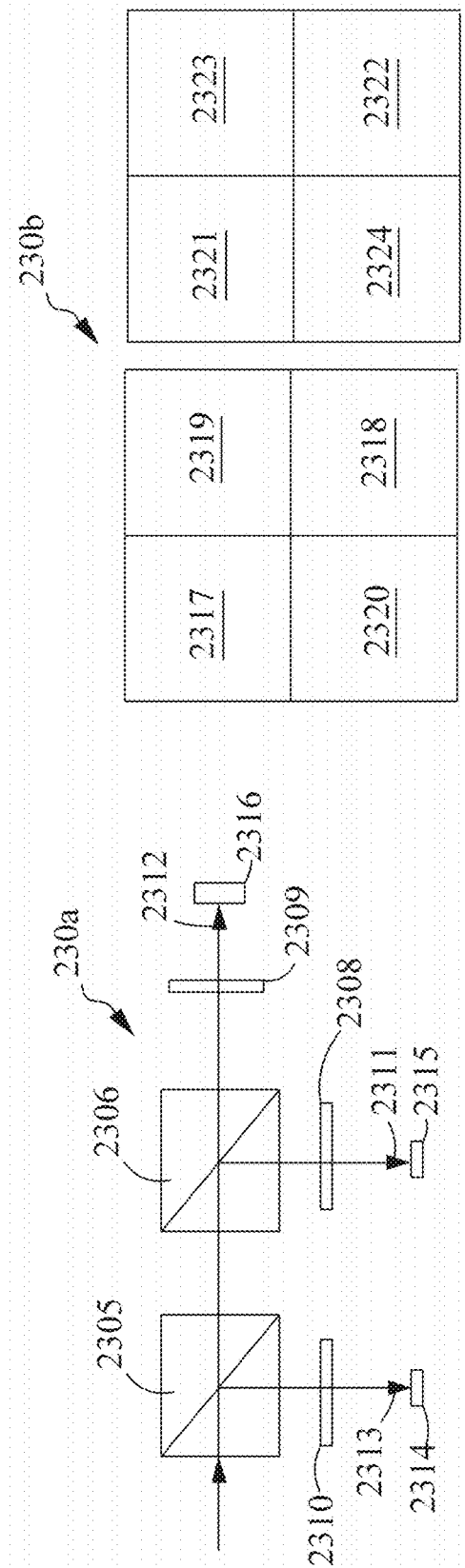
FIG. 2G
FIG. 2H

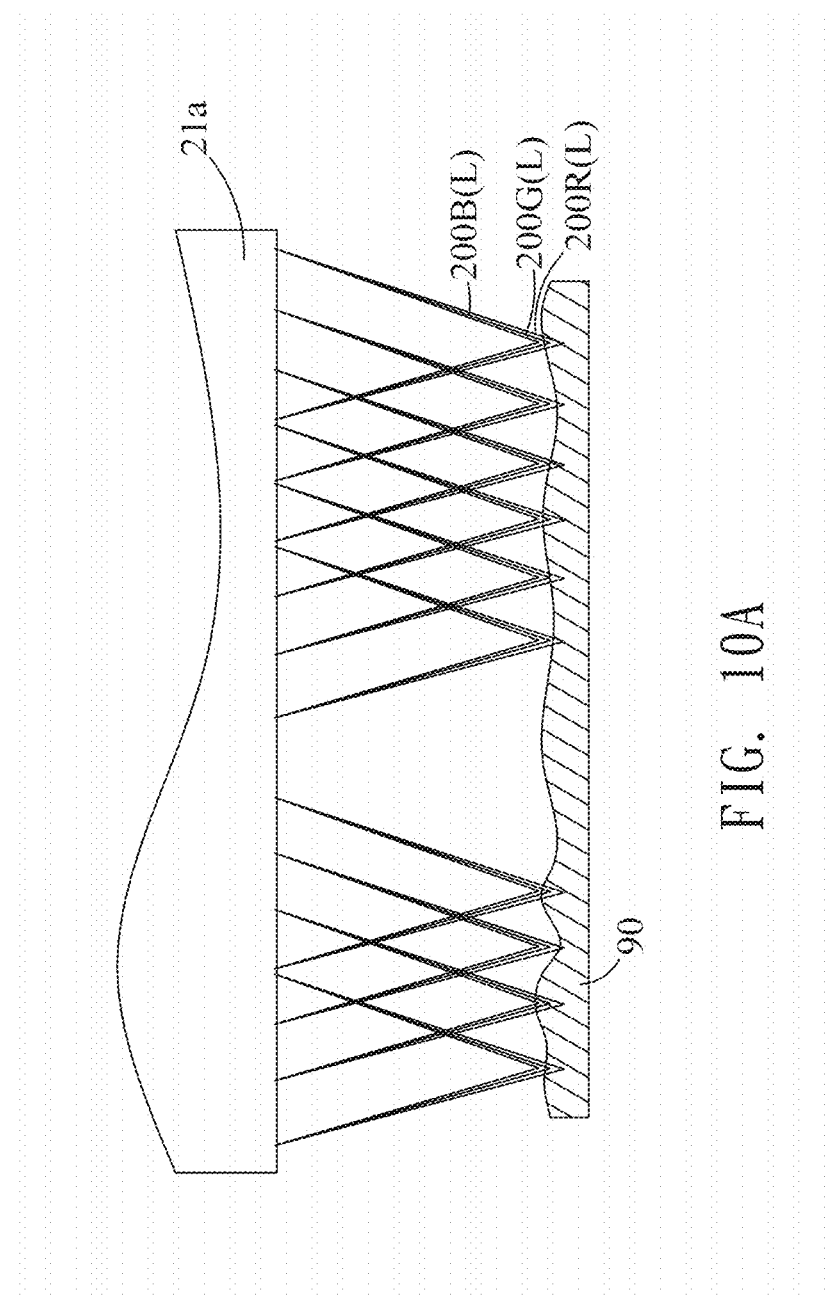

DIFFERENTIAL FILTERING CHROMATIC CONFOCAL MICROSCOPIC SYSTEM

FIELD OF THE INVENTION

The present invention relates to a chromatic confocal measurement and more particularly, to a differential filtering chromatic confocal microscopic system for measuring a surface profile of an object according to two different optical intensities distribution corresponding to two spatial filters, respectively, wherein the two spatial filters have different dimension from each other and being disposed at focal position of the object light passing through the corresponding spatial filter.

BACKGROUND OF THE INVENTION

Conventional confocal chromatic microscope systems are installed on desktop so as to perform a vertical or lateral scan on an object for obtaining a surface profile thereof. Due to the large system volume inducing disadvantages of occupying too much space, various conventional systems are limited to perform surface profile measurement on the object, such as 8-inch wafer having a plurality of large scale integration (LSI) chips formed thereon when the volume or the surface inclined angle of the object is large, thereby reducing practicability and convenience of the entire confiduration.

In the conventional arts, such as US. Pub. No. 2004/0051879, it disclosed a confocal displacement sensor wherein, through an advanced arrangement of optical outputs relative to an imaging optic in the object area of displacement sensor, real images of the optical outputs can be created at different heights. In this art, two measurement beams are created by two planar light sources, and two planar high-resolution cameras are arranged for light intensity detection. The height position of the scanned points of the surface can be calculated and the surface to be measured can be measured simultaneously at a number of scanning points. In addition, it is also known that a color sensing unit is utilized to detect the intensity ration of the object surface, whereby a surface height or depth can be obtained by calculation according to the relationship between color intensity and depth.

However, since the reflection rate with respect to RGB color of the inspection light is varied with the property of object surface, such as color of the object surface, it is necessary to establish a depth relation curve corresponding to the reflection rate of different colors for the surface profile measurement, which is inconvenient for the inspection operator. In addition, another drawback is that the slit structure is indispensable for receiving the object light from the object in the convention configuration, so that a cross talk caused by an overlap between neighboring object lights, such as unfocused lights and stray lights, will be generated inevitably, thereby decreasing effect of image detection resolution.

In addition, US2006/0012871 disclosed a confocal scanning system utilizing pinhole or slit as a confocal aperture for allowing a plurality of laser beams emitted from an illumination unit pass therethrough. The laser beams are then projected onto an object and reflected therefrom. The reflected laser beams pass through the confocal aperture and are guided to the optical detectors.

Furthermore, a "Bipolar absolute differential confocal approach to higher spatial resolution" by Zhao et al. 2004/10/18, Optical Express Vol. 12, No. 21 also disclosed a confocal inspection system for measuring the surface profile of an object, in which two pinholes are respectively arranged before and behind the corresponding collecting lens. In the system, a monochrome laser is projected onto an object through an objective and reflected therefrom for forming an object light. After that, the object light is split into two sub object lights having different optical path from each other and respectively passing through the two pinholes. The two detectors respectively detected the two sub object lights passing through the pinhole thereby obtaining the intensity signals corresponding thereto. The intensity signals are calculated through a differential algorithm for analyzing the surface profile of the object.

Moreover, Taiwan published application TW201321714 also disclosed a chromatic confocal microscope system and signal process method is provided to utilize a first optical fiber module for modulating a light into a detecting light passing through a chromatic dispersion objective and thereby forming a plurality of chromatic dispersion lights to project onto an object. A second optical fiber module conjugated with the first optical fiber module receives a reflected object light for forming a filtered light, which is split into two filtered lights detected by two color sensing units for generating two sets of RGB intensity signals, wherein one set of RGB intensity signals is biased relative to the other set of RGB intensity signals. Then two sets of RGB intensity signals are calculated for obtaining a maximum ratio factor. Finally, according to the maximum ratio factor and a depth relation curve, the surface profile of the object can be reconstructed.

In case of foregoing mentioned system having spatial filters that are arranged before and behind the focal position of the object lights, these conventional system for measuring the surface profile of the object are facing potential problems that are listed below:

(1) Defocus issue: since the object lights are detected by the optical detectors arranged before and behind the focal position, the quality of the images generated from the optical detectors will be reduced thereby increasing the inaccuracy of the inspection.

(2) Inaccuracy of image alignment: since the optical detectors are respectively arranged before and behind the focal position of the object light, the field of view (FOV) of the two optical detectors are different from each other thereby causing inspection inaccuracy.

(3) Inconsistency of spatial resolution: since the optical detectors are respectively arranged before and behind the focal position of the object light, the field of view (FOV) of the two optical detectors are different from each other thereby causing inconsistency of spatial resolution.

(4) Difficult to adjust position of optical detectors: when the chromatic dispersion objective is changed, the whole system should be calibrated especially the position of the two optical detectors, which will increase the inconveniency of the operation of the system.

SUMMARY OF THE INVENTION

The present invention provides a differential filtering chromatic confocal microscopic system, which comprises at least one optical intensity sensing module, each of which further comprises a pair of light intensity sensing devices, a pair of spatial filters respectively corresponding to the pair of light intensity sensing devices and being arranged at the focal position of the two object lights, wherein the two spatial filters having different dimension from each other.

The pair of light intensity sensing devices respectively sensing an object light respectively passing through the pair of spatial filters and then generate corresponding light intensity signal. The light intensity signals corresponding to each light intensity sensing device is utilized for a differential calculation thereby generating two differential rational values corresponding each object light, which are adapted to be a basis of surface profile analysis. In addition to calculating the two differential rational values, the differential calculation can also resolve the issues of uneven brightness generated from the cause that the different inspected positions of the surface of the object having different reflecting rate with respect to the different optical wavelength.

The present invention provides a differential filtering chromatic confocal microscopic system, which modulates a broadband light into a point or linear broadband light for scanning the surface of the object so as to measure the surface profile of the object. By means of a optical intensity sensing module having a pair of light intensity sensing devices, a pair of spatial filters respectively corresponding to the pair of light intensity sensing devices and being arranged at the focal position of the two object lights, wherein the two spatial filters having different dimension from each other such as pinhole diameter or opening width of the slit, and a pair of color filters, each of which is arranged between each light intensity sensing device and corresponding spatial filter and allows a single color spectrum to pass therethrough, two differential rational values of optical intensity corresponding each object light are obtained whereby the problem of cross talk between different color spectrum can be reduced so as to increase accuracy of the surface inspection.

In one exemplary embodiment, the present invention provides a differential filtering chromatic confocal microscopic system, comprising: a light source module, providing a broadband light; a chromatic dispersion objective, axially dispersing the broadband light for forming a plurality of dispersed lights projecting onto an object and reflecting therefrom for forming an object light, wherein the plurality dispersed lights respectively have a specific focal depth different from each other; a first optical modulation module, splitting the object light into a first object light and a second object light; a first optical intensity sensing module, having a pair of first light intensity sensing devices and a pair of first spatial filters having different dimension from each other, wherein one of the first spatial filter is arranged at a focal position of the first object light whereby the first object light passing therethrough is detected by the corresponding first light intensity sensing device thereby obtaining at least one first optical intensity signal while the other first spatial filter is arranged at a focal position of the second object light whereby the second object light passing therethrough is detected by the corresponding first light intensity sensing device thereby obtaining at least one second optical intensity signal; and a signal processing unit, determining depth of at least one measured depth information on the object according to the corresponding at least one second optical intensity signal and at least one second optical intensity signal.

In another exemplary embodiment, the present invention provides A differential filtering chromatic confocal microscopic system, comprising: an light source module, providing a first and a second broadband lights divided from a broadband light; a first and a second spatial filter, respectively receive the first and the second broadband lights, wherein a dimension of each first and the second spatial filter is different from each other; a first optical modulation module, receiving the first and the second broadband lights respectively passing through the first and the second spatial filter, and modulating the first and the second broadband lights into a first and a second polarized lights orthogonal to each other; a chromatic dispersion objective, axially dispersing the first and the second polarized lights for forming a plurality of first dispersed lights and a plurality of second dispersed lights projecting onto an object and reflecting therefrom for forming a first and a second polarized object lights having the same optical path, wherein the plurality of first dispersed lights respectively have a first specific focal depth different from each other while and the plurality of second dispersed lights respectively have a second specific focal depth different from each other; a second optical modulation module for splitting the first and the second polarized object lights having the same optical path into the first and the second polarized object lights having different optical path; a pair of light intensity sensing devices, wherein one of the pair of the light intensity sensing devices detects the first polarized object light for generating at least one first optical intensity signal corresponding to an inspection location of the object while the other one of the pair of the light intensity sensing devices detects the second polarized object light for generating at least one second optical intensity signal corresponding to the at least one first optical intensity signal; and a signal processing unit, determining depth of at least one inspected position on the object according to the at least one first optical intensity signal and the at least one second optical intensity signal.

BRIEF DESCRIPTION OF THE DRAWINGS

The present disclosure will become more fully understood from the detailed description given herein below and the accompanying drawings which are given by way of illustration only, and thus are not limitative of the present disclosure and wherein:

FIGS. 2B and 2C respectively illustrates spatially filtering under different spatial filters having different structure and dimension;

FIGS. 2E to 2H respectively illustrates different types of light intensity sensing devices according to different embodiments of the present invention;

FIGS. 10A and 10B illustrate a linear broadband light according to an embodiment of the present invention;

DETAILED DESCRIPTION OF THE INVENTION

For your esteemed members of reviewing committee to further understand and recognize the fulfilled functions and structural characteristics of the disclosure, several exemplary embodiments cooperating with detailed description are presented as follows.

Figure 1:
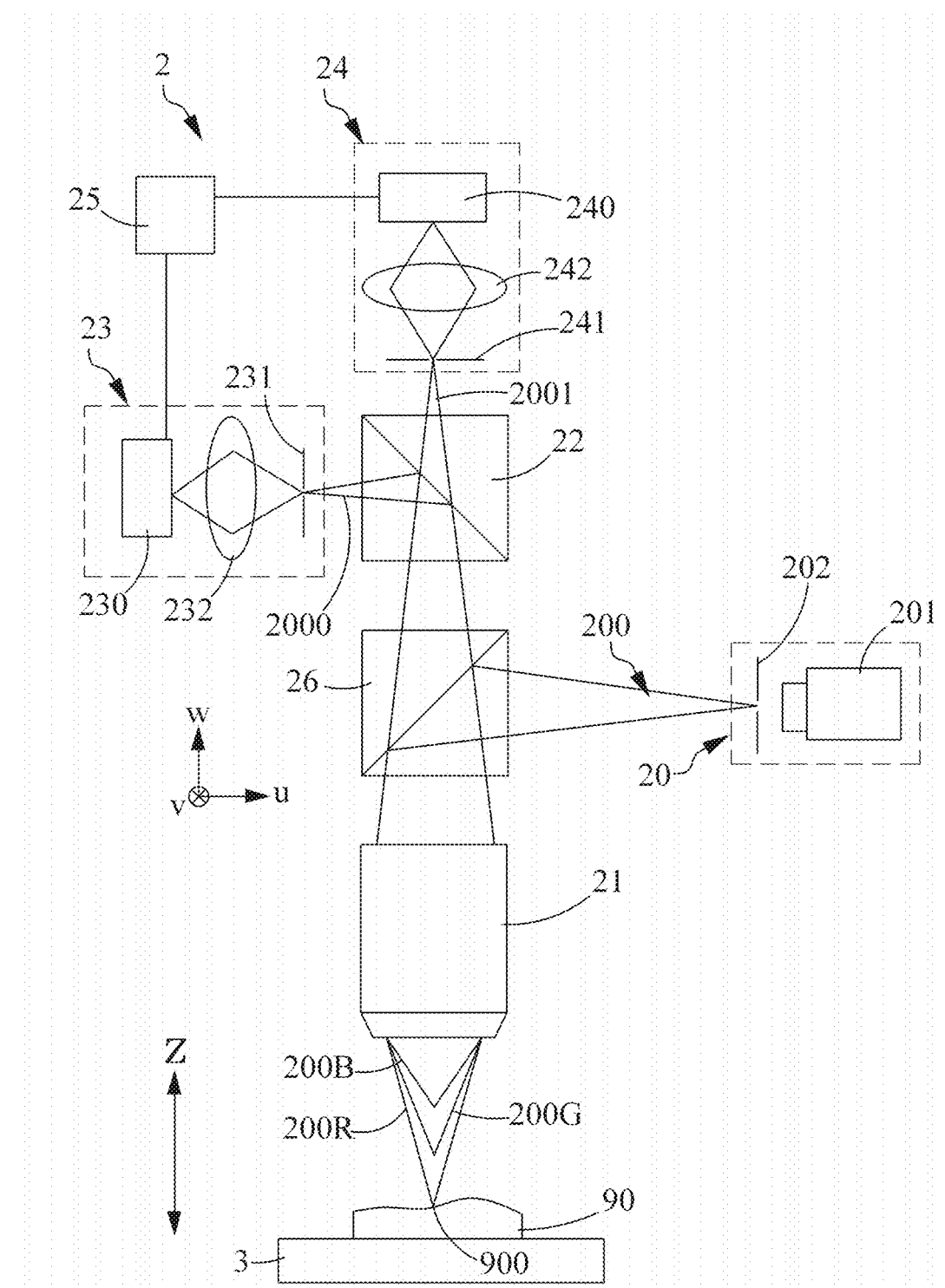
FIG. 1 illustrates a differential filtering chromatic confocal microscopic system according to a first embodiment of the present invention.

Please refer to FIG. 1 which illustrates a differential filtering chromatic confocal microscopic system according to a first embodiment of the present invention. In the present embodiment, the differential filtering chromatic confocal microscopic system 2 comprises a light source module 20, a chromatic dispersion objective 21, a first optical modulation module 22, and a pair of first optical intensity sensing module 23 and 24, and a signal processing unit 25. The light source module 20 provides a broadband light 200, which can be, but should not limited to, single color light having a specific bandwidth such as red light (620 nm~750 nm), green light (495 nm~570 nm), or blue light (476~495 nm). Alternatively, in another embodiment, the broadband light 200 can also be a composite light having a plurality of color spectrum, such as a white light having wavelength spectrum ranging from 380 nm to 750 nm. In the present embodiment, the broadband light is a white light.

In addition, the light source module 20 further comprises a light generating device 201 and a shaping element 202, wherein the light generating device 201 generates the broadband light 200 which is a composite light having a plurality of color spectrum, such as white light. The shaping element 202 is utilized to modulate the broadband light 200 into a point broadband light or a linear broadband light having a focal position. The shaping element 202 can be, but should not be limited to, a slit structure or a pinhole structure for spatially shaping the broadband light 200. In the present embodiment, the broadband light 200 is a point broadband light. In addition, it is noted that the single color light can be generated by arranging a color filter at a position between the light generating device 201 and the shaping element 202, wherein the color filter allows lights having a specific wavelength spectrum such as red light (620 nm~750 nm), green light (495 nm~570 nm), or blue light (476~495 nm) to pass therethrough.

The spatially filtered broadband light 200 is further guided to enter the chromatic dispersion objective 21 through a first beam splitter 26 arranged at the optical path of the broadband light 200. The chromatic dispersion objective 21 axially disperses the filtered broadband light 200 for forming a plurality of dispersed lights 200R, 200G, and 200B. Each dispersed lights 200R, 200G and 200B has a specific wavelength for forming a continuous spectrum. In the present embodiment, the chromatic dispersion objective 21 has at least two chromatic aberration lenses which are adapted to axially disperse the broadband light 200 thereby generating the plurality of dispersed lights which are labeled as three exemplary notations 200R, 200G, and 200B.

The plurality of dispersed lights 200R, 200G, and 200G are projected onto the object 90 arranged on a moving platform 3 which can perform a Z-direction translation. In addition, the moving platform 3 can also perform a XY planar translation by X-direction and Y-direction driving devices such as a combination of motor, screw and guide rail known in the art.

The plurality of dispersed lights projecting onto the object 90 are immediately reflected from the surface of the object 90 thereby forming an object light. The object light passes through the first beam splitter 26 and are guided into the first optical modulation module 22 whereby the object light is split into a first object light 2000 and a second object light 2001. The first optical modulation module 22, in the present embodiment, is a beam splitter. Please refer to FIG. 2A, which illustrates the dispersed lights 200R, 200G, and 200B projecting onto the surface of object. Taking white light as an example of the broadband light, since white light has a continuous spectrum formed by a plurality of color lights, when the white light is dispersed, the plurality of dispersed lights, which are represented as 200R (red light), 200G (green light), and 200B (blue light), respectively have a specific focal depth different from each other. Generally speaking, the dispersed light having shorter wavelength or higher frequency has small focal depth whereas the dispersed light having larger wavelength or lower frequency has large focal depth. Accordingly, when the plurality of dispersed lights are reflected from the surface of object 90, the reflection area of each of the plurality of dispersed lights from the object surface is different from each other.

Figure 2A:
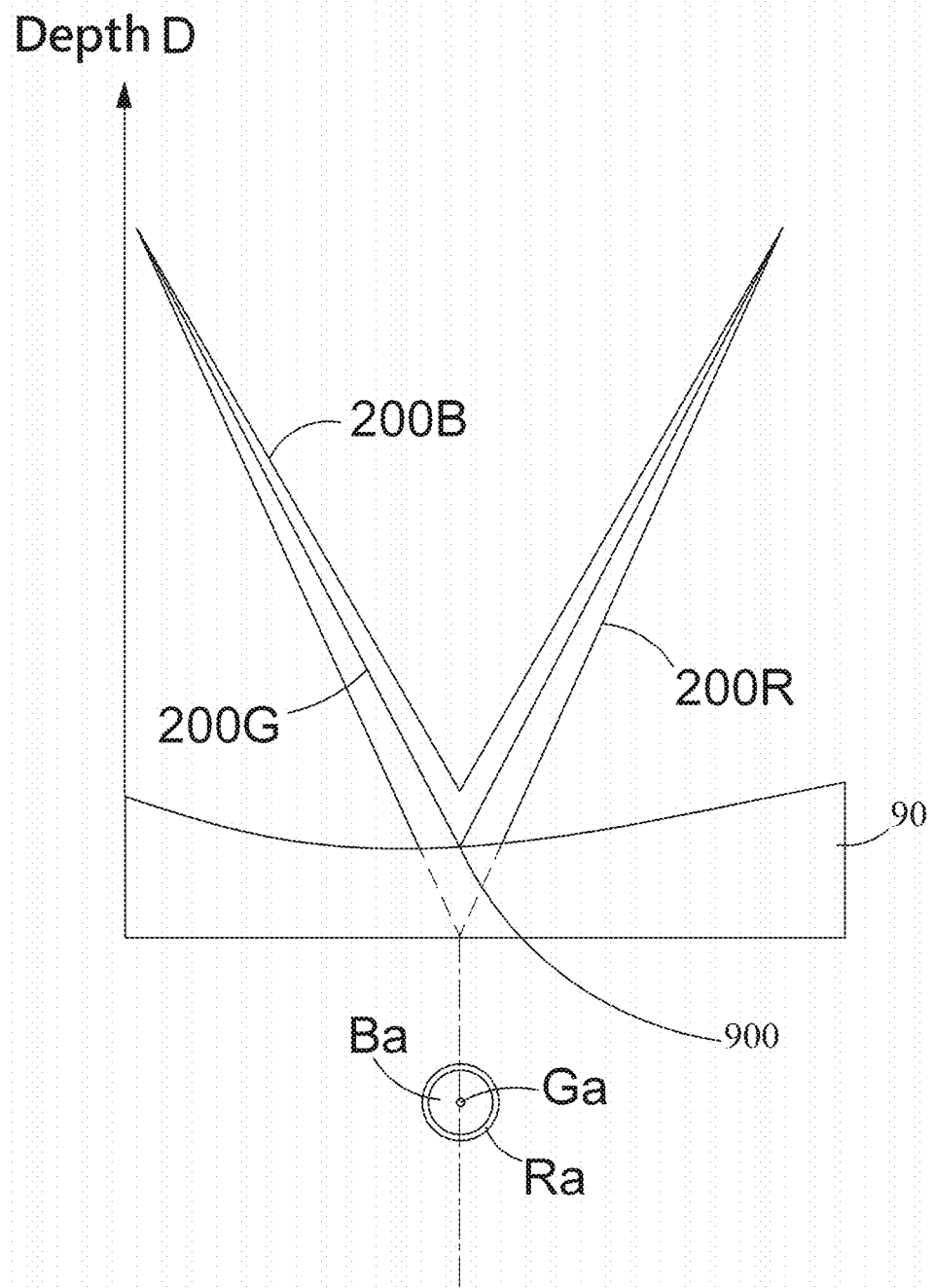
FIG. 2A schematically shows a dispersed broadband light projecting onto the object.

In FIGS. 2A and 2B, at position 900 on the surface of the object 90, the focal position of green dispersed light 200G is around the position 900, while the other dispersed lights such as the red dispersed light 200R or blue dispersed light 200B are focused before or behind the position 900 such that the optical intensity distribution area of each dispersed light 200R, 200G, and 200B is different from the other, wherein Ga represents the optical intensity distribution area of the green light component of the first and second object light, Ra represents the optical intensity distribution area of the red light component of the first and second object light, and Ba represents the optical intensity distribution area of the blue light component of the first and second object light.

Please refer back to FIG. 1. Thereafter, the split first and second object light 2000 and 2001 from the first optical modulation module 22 are detected by the pair of optical intensity sensing modules 23 and 24. Each of the optical intensity sensing module 23 or 24 comprises a first light intensity sensing device 230 or 240, and a first spatial filter 231 or 241, wherein the first spatial filter 231 is arranged at a focal position of the first object light 2000 while the other first spatial filter 241 is arranged at a focal position of the second object light 2001 and the dimension of the first spatial filters 231 and 241 are different from each other. It is noted that the definition of dimension of the first spatial filters 231 and 241 are different according to the structure of the first spatial filters 231 and 241. For example, in one embodiment, when first spatial filters 231 and 241 are the slit structure, the dimension thereof refers to the opening width of the slit structure whereas, in alternative embodiment, when first spatial filters 231 and 241 are the pinhole structure, the dimension thereof refers to the diameter of the pinhole structure. In addition, the first spatial filters 231 and 241 are also selected to fit the condition of the shape of broadband light 200. If the broadband light 200 is a point broadband light, then the first spatial filters 231 and 241 are selected to be the pinhole structure. Alternatively, if the broadband light 200 is a linear broadband light, then the first spatial filters 231 and 241 are selected to be the slit structure.

In the present embodiment, the first object light 2000 is focused onto the first spatial filter 231 and is spatially filtered by the first spatial filter 231. The filtered first object light 2000 passes through a collecting element 232 and then is focused onto the first light intensity sensing device 230. On the other hand, the second object light 2001 is focused onto the first spatial filter 241, and is spatially filtered by the first spatial filter 241. The filtered second object light 2001 passes through a collecting element 242 and then is focused onto the first light intensity sensing device 240. It is noted that the collecting element 232 can be a single lens or be formed by a plurality of lens. Please refer to FIGS. 2B and 2C, which illustrate the filtered object light passing through the first spatial filter. In FIG. 2B, the first spatial filter is a pinhole structure 231a and 241a, wherein the diameter of pinhole structure 231a is larger than the diameter of pinhole structure 241a, while in FIG. 2C, the spatial filter is a slit structure 231b and 241b, wherein the opening width of slit structure 231b is larger than the slit structure 241b.

Figure 2D:
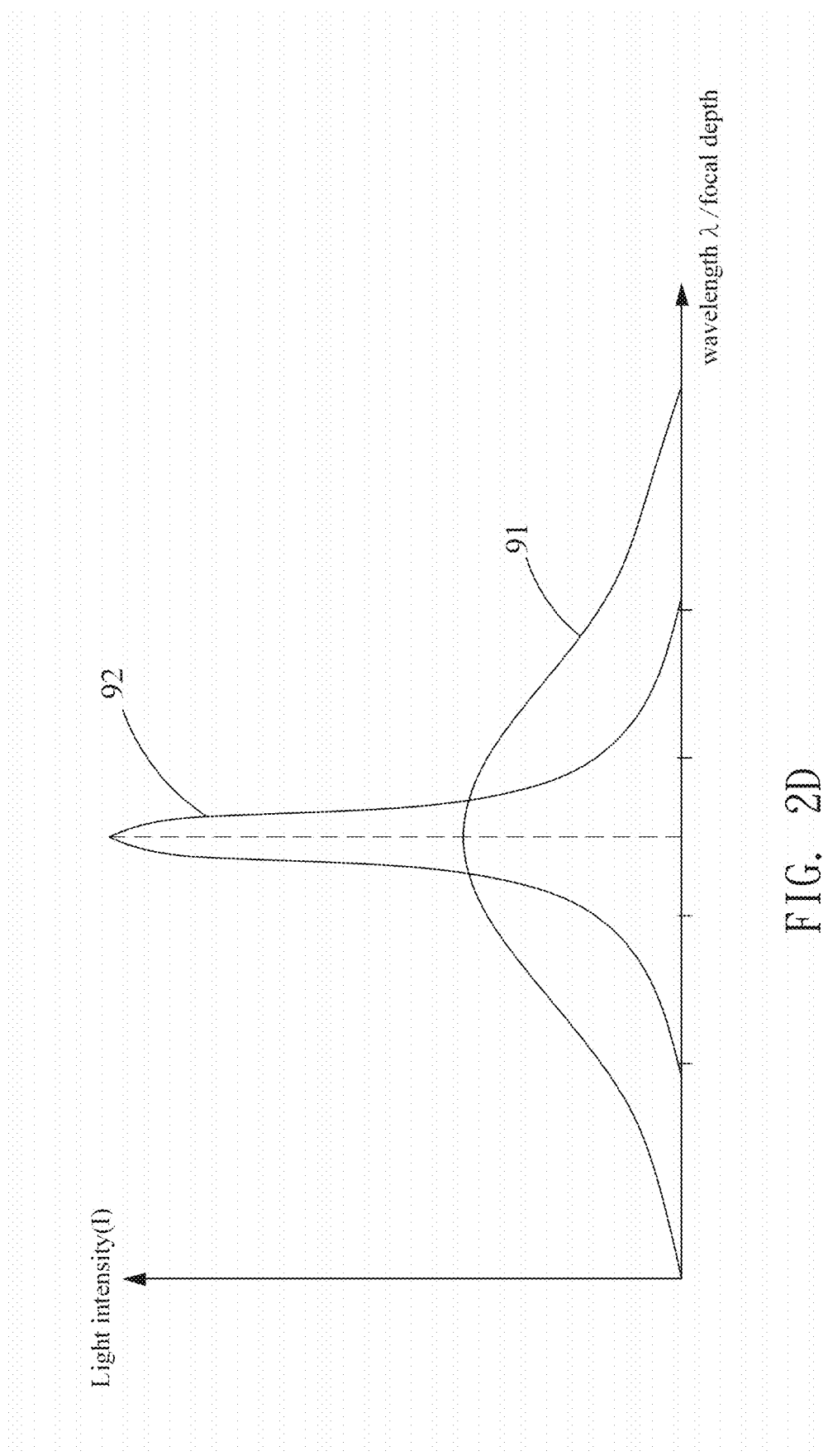
FIG. 2D illustrate a relationship of optical intensity and wavelength after the first and second object lights respectively passing through the spatial filter arranged at the corresponding optical path.

Please refer FIGS. 1 and 2D, wherein FIG. 2D illustrates the relation between optical intensity and wavelength of the first and second object lights passing through the first spatial filter. In the present embodiment, the first spatial filters 231 and 241 are pinhole structure in which the diameter of first spatial filter 231 is larger the diameter of first spatial filter 241. Due to the size of pinhole structure is different, the wavelength range of the first and second object lights allowed to pass the first spatial filters 231 and 241 are different from each other. For example, for the pinhole having large diameter, the wavelength range of the first object light allowing to passing the large pinhole is broadly distributed so that the optical intensity curve 91 will have gentle slope and wide wavelength range distribution whereas, for the pinhole having small diameter, the wavelength range distribution of the second object light allowing to pass the small pinhole is concentratedly distributed so that the optical intensity curve 92 will have a rapid slope thereby making the optical intensity curve 92 exhibits like a peak curve having a maximum optical intensity larger than the maximum optical intensity of the optical intensity curve 91. It is noted that since the first spatial filters 231 and 241 are respectively arranged at focal position of the first and second object lights, the wavelength λ corresponding to the maximum optical intensity of the first and second object lights passing through the first spatial filter are the same as each other. The wavelength having maximum optical intensity represents the wavelength of the dispersed light focused onto and reflected from the focal point of the object 90, i.e. the inspected position 900 illustrated in FIG. 2A.

When the first light intensity sensing device 230 detects the first object light 2000 passing through the first spatial filter 231, it will generate a first optical intensity signal corresponding to the inspected position. Meanwhile, the first light intensity sensing device 240 detects the second object light 2001 passing through the first spatial filter 241 thereby generating a second optical intensity signal corresponding to the same inspected position.

Figure 2E:
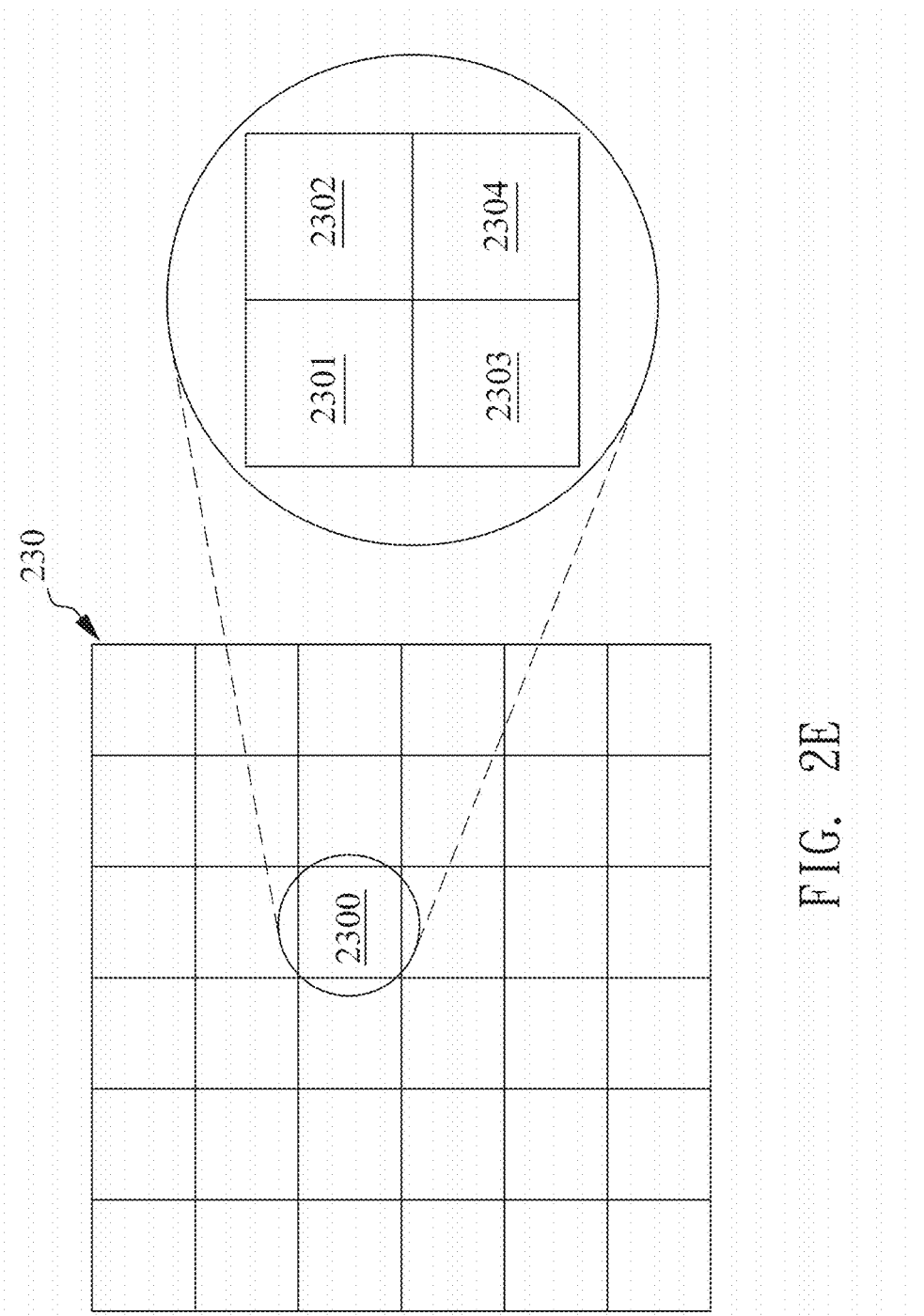

Please refer to FIGS. 2D to 2H, which respectively illustrate different type of light intensity sensing devices according to the embodiments of the present invention. Since the light intensity sensing devices 230 and 240 are the same, the light intensity sensing device is explained by taking the first light intensity sensing device 230 shown in FIG. 1 as an example for explanation, In the present embodiment, the first light intensity sensing device 230 is a color light intensity sensing device such as color CCD, which has different kinds of design in response to the various type of light source. The FIG. 2E illustrates a planar type of color CCD having a plurality of sensing units 2300 arranged two-dimensionally. Each sensing unit 2300 comprises a plurality of sensing elements 2301~2304, each of which has a color filter corresponding to a specific color spectrum disposed thereon. For example, the sensing elements 2301 and 2304 respectively have color filter allowing lights having a green color spectrum (495 nm~570 nm) to pass therethrough, sensing element 2302 has a color filter allowing lights having a red color spectrum (620 nm~750 nm) to pass therethrough, and the sensing element 2303 has a color filter allowing lights having a blue color spectrum (476 nm~495 nm) to pass therethrough. When the first object light 2000 passes through the first spatial filter 231, the relation between wavelength distribution and optical intensity will be like the optical intensity curve 91. When the filtered first object light enters the light intensity sensing device 230, it will pass through the color filters of the sensing elements 2301~2304 and then detected by the sensing elements 2301~2304, thereby generating optical intensity signals of red, green and blue lights.

Please refer to FIG. 2F, which illustrates another exemplary embodiment of the light intensity sensing device. In the present embodiment, the light intensity sensing device 230a comprises three linear sensing units respectively having a color filter, each of which allows lights having a spectrum such as red light spectrum, green light spectrum or blue light spectrum to pass therethrough, and a plurality of sensing elements arranged one-dimensionally for detecting the lights passing through the corresponding color filter. The lights passing through the first spatial filter is corresponding to the curve 91 illustrated in FIG. 2D and are detected by the linear type light intensity sensing device 230a thereby generating optical intensity signal of red, green and blue lights.

Please refer to FIG. 2G, which illustrates another embodiment of the light intensity sensing device in the present invention. In this embodiment, the first light intensity sensing device 230b is a point type light intensity sensing device having beam splitting elements 2305 and 2306 for sequentially dividing the reflected object light from the object having optical intensity distribution illustrated as curve 91 shown in FIG. 2D into three sub object lights. The three sub object lights are guided to pass through color filter 2308 corresponding to red light spectrum, color filter 2309 corresponding to green light spectrum and color filter 2310 corresponding to blue light spectrum, respectively thereby forming object light 2311 having red light spectrum, object light 2312 having green light spectrum, and object light 2313 having blue light spectrum. Thereafter, the filtered object lights 2311~2313 are respectively detected by light sensing elements 2314~2316 thereby generating optical intensity signal of red, green and blue lights.

Alternatively, another point type of light intensity sensing device is illustrated in FIG. 2H. In the present embodiment, there has two main parts in the point type light intensity sensing device, wherein the first part is light sensing unit, and the second part is the filter unit. The light sensing unit comprises a plurality of light sensing elements 2317~2320 and the filter unit comprises a plurality of color filters 2321~2324 respectively corresponding the plurality of light sensing elements 2317~2320 wherein the color filter 2323 allows lights having red light spectrum to pass therethrough, the color filters 2321 and 2322 allow lights having green light spectrum to pass therethrough, and the color filter 2324 allows lights having blue light spectrum to pass therethrough so that the object light will be modulated into red light, green light and blue light after passing through the color filters 2321~2324. The red, green, and blue lights then are respectively detected by the corresponding sensing devices 2317~2320 thereby generating optical intensity signal of red, green and blue lights. It is noted that the foregoing embodiments in FIGS. 2E~2H are explained by taking first light intensity sensing device 230 and filtered first object light 2000 shown in FIG. 1 as examples; likewise, the first light intensity sensing device 240 has the same configuration as the embodiments shown in FIGS. 2E~2H, which can be utilized to detect the filtered second object light 2001 having the intensity distribution curve 92 shown in FIG. 2D thereby generating the optical intensity signal of red, green and blue lights.

In addition, in order to prevent the inaccuracy issue arises from a cause that the optical intensity signals generated from the optical sensing devices 230 and 240 have different maximum intensity due to the dimension differences between the first spatial filters 231 and 241, a first signal process, a normalization procedure, is further performed in the signal processing unit 25 to process the two sets of optical intensity signal of red, green and blue lights respectively corresponding to the light intensity sensing devices 230 and 240 whereby the magnitude of each optical intensity signals of red, green and blue lights is normalized within a range between 0 and 1.

The normalized first and second optical intensity signals respectively corresponding to the first optical sensing device 230 and 240 are further processed to determining surface depth by the signal processing unit 25 according to a relation between a signal intensity ratio and object surface depth stored therein. In the determining surface depth process, the signal processing unit 25 performs a second signal process on the first optical intensity signal and the corresponding second optical intensity signal so as to obtain a first differential rational value of optical intensity, and then determine a depth of the inspected location corresponding to the first differential rational value of optical intensity according to the relation between the signal intensity ratio and object surface depth.

First, the signal process performed by the signal processing unit 25 includes the first signal process which is the normalization procedure, and the second signal process which is a differential calculation between the first and second optical intensities are explained below. In the embodiment that each first light intensity sensing device 230 or 240 is a color CCD, the R, G and B color intensities contained within first optical intensity signal and second optical intensity signal, respectively acquired by the first light intensity sensing device 230 and 240 can be expressed by the following Equations (1-1), (1-2), and (1-3), wherein Ir, Ig, and Ib respectively refer to a normalization distribution of the R, G, B lights detected by the color CCD where the intensity distribution of the three color lights will be varied associated with the depth of the surface of the object.

$$I_r(v,w_s,u) = \{S_{r\lambda}(v,w_s) \otimes |h_{r\lambda}(v,w,u)|^2\} \{D_{r\lambda}(v,w) \otimes |h_{r\lambda}(v,w,u)|^2\} \quad (1-1)$$

$$I_g(v,w_s,u) = \{S_{g\lambda}(v,w_s) \otimes |h_{g\lambda}(v,w,u)|^2\} \{D_{g\lambda}(v,w) \otimes |h_{g\lambda}(v,w,u)|^2\} \quad (1-2)$$

$$I_b(v,w_s,u) = \{S_{b\lambda}(v,w_s) \otimes |h_{b\lambda}(v,w,u)|^2\} \{D_{b\lambda}(v,w) \otimes |h_{b\lambda}(v,w,u)|^2\} \quad (1-3)$$

In addition, in the above Equations 1-1, 1-2, and 1-3, $r_\lambda$ refers to the range of the wavelength that is allowed to pass through the red color filter within the color CCD, $g_\lambda$ refers to the range of the wavelength that is allowed to pass through the green color filter within the color CCD, and $b_\lambda$ refers to the range of the wavelength that is allowed to pass through the blue color filter within the color CCD. The subscript s refers to the different dimension of the spatial filters 231 and 241 illustrated in the FIG. 1. Moreover, the notation u, v, and w respectively represent a three-dimensional axis spatially formed with respect to the optical axis of the first and second object lights 2000 and 2001 shown in FIG. 1, wherein v represents a direction vertically entering the drawing of FIG. 1.

It is noted that, in the Equations 1-1, 1-2, and 1-3, the intensity distribution Ir, Ig and Ib respectively corresponding to R, G, and B lights reflected from the object surface are formed without a consideration of surface reflecting rate of the object. Accordingly, in order to enhance the accuracy of the inspection, the issue of reflecting rate of the object with respect to the R, G and B lights is considered by rewriting the intensity distribution Ir, Ig and Ib acquired by the color CCD as Equations 1-4, 1-5, and 1-6 shown below, wherein $n_r$, $n_g$, and $n_b$, respectively, refer to the reflecting rate of the object with respect to R, G, and B lights while s represents spatial filter 231 and 241.

$$I'_r(v,w_s,u) = n_r I_r(v,w_s,u) \quad (1-4)$$

$$I'_g(v,w_s,u) = n_g I_g(v,w_s,u) \quad (1-5)$$

$$I'_b(v,w_s,u) = n_b I_b(v,w_s,u) \quad (1-6)$$

After obtaining normalized optical intensity signal, the differential calculation is performed to obtain the differential rational values of optical intensity of each color light. The differential rational value of optical intensity for each color light such as R, G, and B light can be expressed as the Equation 1-7, which is referred to the differential rational value of optical intensity of red light, Equation 1-8, which is referred to the differential rational value of optical intensity of green light, and Equation 1-9 which is referred to the differential rational value of optical intensity of blue light, wherein $I'_r(v, w_1, u)$ and $I'_r(v, w_2, u)$ are respectively referred to the optical intensity of red light within the first optical intensity signal detected by the first light intensity sensing device 230 and optical intensity of red light within the second optical intensity signal detected by the second light intensity sensing device 240, $I'_g(v, w_1, u)$ and $I'_g(v, w_2, u)$ are respectively referred to the optical intensity of green light within the first optical intensity signal detected by the first light intensity sensing device 230 and optical intensity of green light within the second optical intensity signal detected by the second light intensity sensing device 240, and $I'_b(v, w_1, u)$ and $I'_b(v, w_2, u)$ are respectively referred to the optical intensity of blue light within the first optical intensity signal detected by the first light intensity sensing device 230 and optical intensity of blue light within the second optical intensity signal detected by the second light intensity sensing device 240, while $w_1$ and $w_2$ are referred to the spatial filters 231 and 241 arranged corresponding to the light intensity sensing devices 230 and 240, respectively.

It is noted that the reflecting rates $n_r$, $n_g$, and $n_b$ within the Equations 1-4, 1-5, and 1-6 are eliminated in the differential Equations 1-7, 1-8, and 1-9, which means that the differential rational value of optical intensity of each color light has no relation with the reflecting rates $n_r$, $n_g$, and $n_b$. Therefore the $RC_R$, $RC_G$ and $RC_B$ respectively calculated from Equations 1-7, 1-8, and 1-9 can be referred to the differential rational values of optical intensity of inspected position 900 of object shown in FIG. 1.

$$RC_R(v, w, u) = \frac{I'_r(v, w_1, u) - I'_r(v, w_2, u)}{I'_r(v, w_1, u) + I'_r(v, w_2, u)} \quad (1\text{-}7)$$
$$= \frac{n_r(w)I_r(v, w_1, u) - n_r(w)I_r(v, w_2, u)}{n_r(w)I_r(v, w_1, u) + n_r(w)I_r(v, w_2, u)}$$
$$= \frac{I_r(v, w_1, u) - I_r(v, w_2, u)}{I_r(v, w_1, u) + I_r(v, w_2, u)},$$

$$RC_G(v, w, u) = \frac{I'_g(v, w_1, u) - I'_g(v, w_2, u)}{I'_g(v, w_1, u) + I'_g(v, w_2, u)} \quad (1\text{-}8)$$
$$= \frac{n_g(w)I_g(v, w_1, u) - n_g(w)I_g(v, w_2, u)}{n_g(w)I_g(v, w_1, u) + n_g(w)I_g(v, w_2, u)}$$
$$= \frac{I_g(v, w_1, u) - I_g(v, w_2, u)}{I_g(v, w_1, u) + I_g(v, w_2, u)},$$

$$RC_B(v, w, u) = \frac{I'_b(v, w_1, u) - I'_b(v, w_2, u)}{I'_b(v, w_1, u) + I'_b(v, w_2, u)} \quad (1\text{-}9)$$
$$= \frac{n_b(w)I_b(v, w_1, u) - n_b(w)I_b(v, w_2, u)}{n_b(w)I_b(v, w_1, u) + n_b(w)I_b(v, w_2, u)}$$
$$= \frac{I_b(v, w_1, u) - I_b(v, w_2, u)}{I_b(v, w_1, u) + I_b(v, w_2, u)},$$

Figure 3:
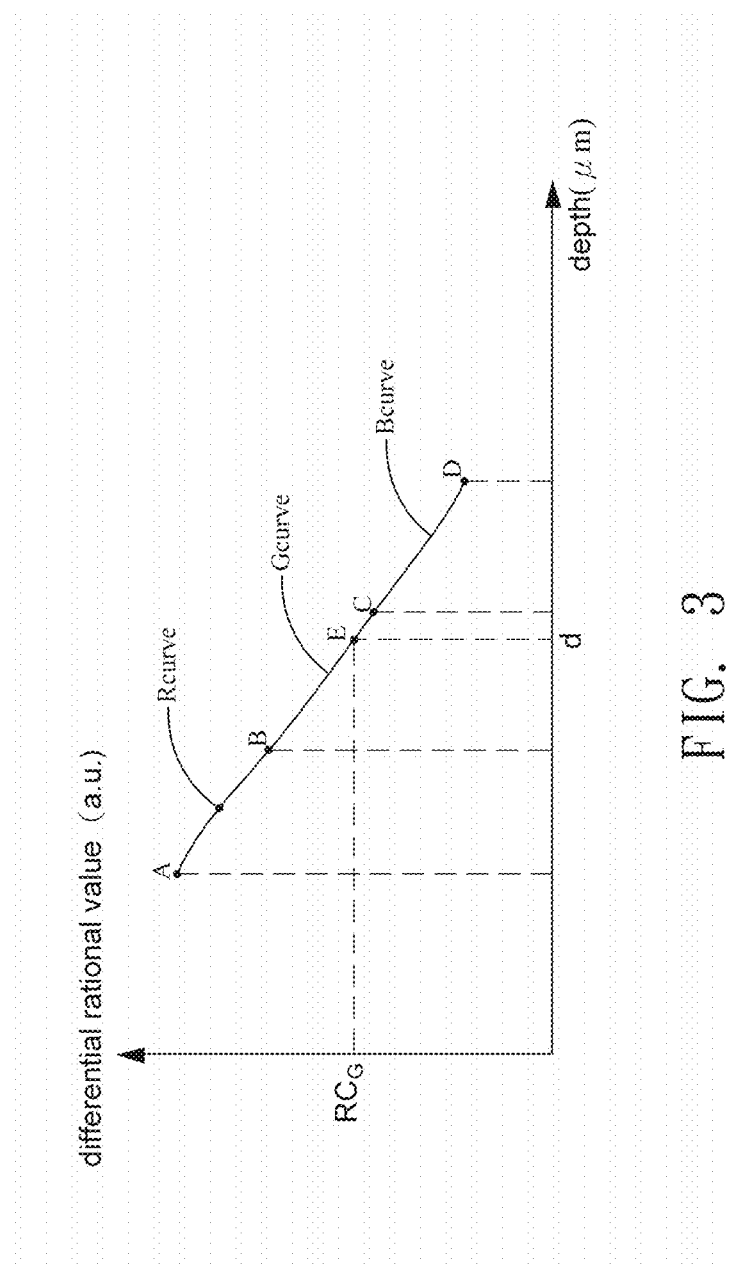
FIG. 3 illustrates depth relation range by combining linear part of depth curve of RGB lights.

Please refer to FIG. 3, which illustrates depth relation range by combining linear part of depth curve of RGB lights, wherein the segment AB represents the depth curve of R light, segment BC represents depth curve of green light, and segment CD represents the depth curve of blue light, and the horizontal axis represents the object surface depth while the vertical axis represents the differential rational value of optical intensity. After obtaining the differential rational values of optical intensity $RC_R$, $RC_G$, and $RC_B$, a surface depth of the inspected position can be looked up according to the depth curve shown in FIG. 3. In the present embodiment, the differential value $RC_G$ can be looked up at location E of segment BC whereby the surface depth d of the inspected position 900 corresponding to the surface of the tested object is obtained. It is noted that the shape of the broadband light is a point shape; therefore, it is capable of measuring another location of surface of the object by changing the inspected position of the broadband light through moving the platform 3 shown in FIG. 1.

Figure 4:
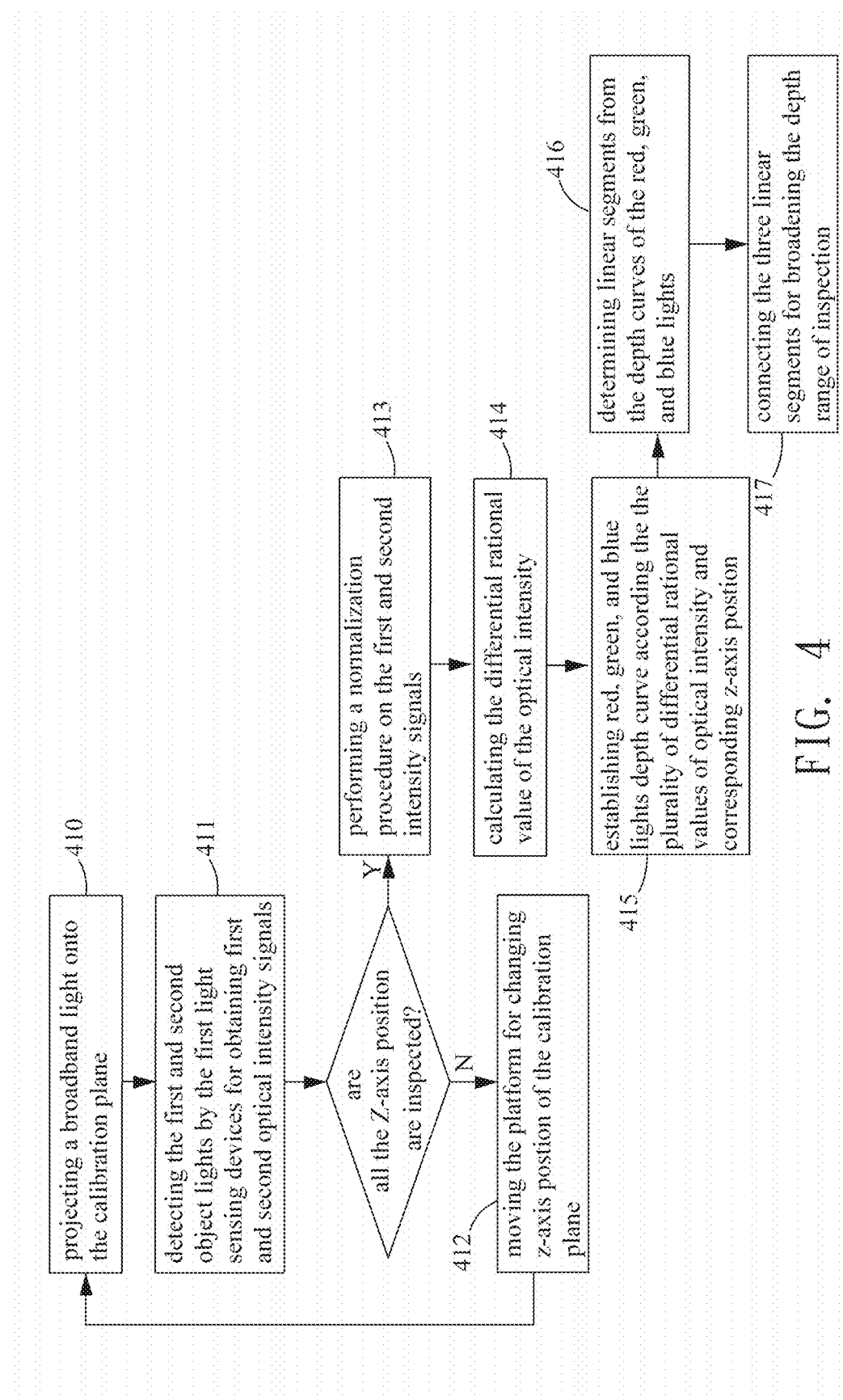
FIG. 4. illustrates a flow chart for establishing a depth curve.

Next, please refer to FIG. 4, which illustrates a flow chart for establishing a depth curve for a differential filter chromatic confocal microscopic system such as the system shown in FIG. 1. First, a step 410 is performed to arrange a calibration plane onto the moving platform 3, which is located at a specific height in z-axis. Then, the broadband light 200 is projected on an inspected position of the calibration plane thereby forming a plurality of object lights having different focal depth, respectively. Next, in step 411, the plurality of object lights are guided to be detected by the first optical intensity sensing module 23, and 24, in which, the plurality of object lights are divided into two sub object lights respectively passing through the spatial filters 231 and 241, and are detected by the first light intensity sensing device 230 and 240, respectively, whereby a first and second optical intensity signals are obtained. In the present embodiment, the first and second optical intensity signals all comprise a red light intensity value, a green light intensity value, and a blue light intensity value, respectively.

After that, a step 412 is performed to change the z-axis location by moving the platform 3 along z-axis. In one embodiment, the step 412 can be achieved though a piezoelectric element, which can be controlled to move the platform 3 at nanometer level. Following the step 412, the flow returns to steps 410 and will repeat the steps 410-412 until all the locations along z-axis are inspected. After inspecting all the locations along z-axis, the flow goes to step 413, in which a normalization process is performed for processing the plurality of first and second optical intensity signals so that the magnitude of R light intensity, G light intensity and B light intensity of each first and second optical intensity signals are normalized to be within a range between 0 and 1. The algorithm of normalization process is well known by the one having ordinary skilled in the art, which will not be explained hereinafter. Thereafter, a step 414 is performed to calculate differential rational values of optical intensity, $RC_R$, $RC_G$, and $RC_B$ according to Equations 1-7, 1-8, and 1-9, respectively. Since the z-axis location of the platform is known, each calculated differential rational value of optical intensity corresponding to each specific z location are utilized to form a depth curve of red light, depth curve of green light and depth curve of blue light shown in FIG. 5.

Figure 5:
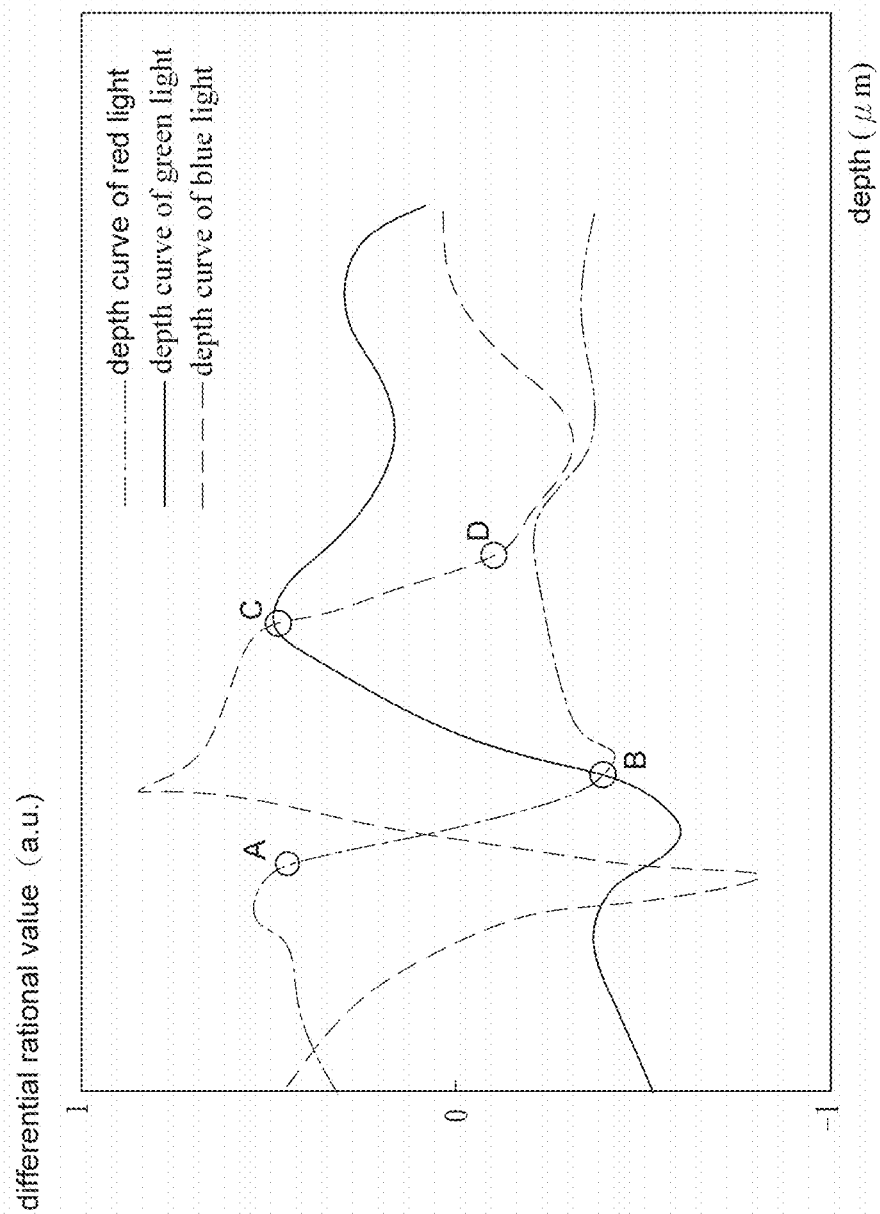
FIG. 5 illustrates depth curves of RGB lights.

Please refer to FIGS. 4 and 5, after the step 415, step 416 is performed to determine a linear segment AB from the depth curve of red light, a linear segment BC from the depth curve of green light, and a linear segment CD from the depth curve of blue light, wherein the points B and C are intersection between the depth curves. In order to combine the determined linear segments AB, BC, and CD for obtaining a broad linear range of surface depth, a step 417 is performed to interconnect the linear segment AB, BC, and CD according to Equation 1-10, whereby the depth curve shown in FIG. 3 can be formed.

$$\Gamma(u) = \begin{cases} \Gamma(u_1) & u = u_1 \leftarrow AB \\ \Gamma_B + \{\Gamma_B - \Gamma(u_2)\} & , u = u_2 \leftarrow BC \\ \{\Gamma(u_3) - \Gamma_C\} + \{\Gamma_B + (\Gamma_B - \Gamma_C)\} & u = u_3 \leftarrow CD \end{cases} \quad (1\text{-}10)$$

In Equation 1-10, $\Gamma$ represents rational value of optical intensity of each depth curve associated with R, G, and B lights, while u represents segments AB, BC, and CD shown in FIG. 3. It is noted that the normalization process in the step 413 is not necessary, which can be executed according to the need. In addition, if the normalization step 413 is adapted, the difference between the light intensity sensing devices are eliminated whereby it is not necessary to perform calibration process even if the light intensity sensing devices are changed in future so as to efficiency of inspection.

In the embodiment shown in FIG. 1, two spatial filters such as slit structure having different opening width or pinhole structure having different pinhole diameter are respectively arranged in front of the light intensity sensing devices whereby two sets of depth curves of RGB lights having different FWHM value can be obtained. It is noted that although there will have color filters arranged within the light intensity sensing device (color CCD) for isolating R light, G light and B light, the color filters still can't independently and completely isolate the RGB lights because the wavelength spectrum of red light allowed to pass through the red color filter will partially covered the wavelength spectrum of green light, and the wavelength spectrum of green light allowed to pass through the green color filter will partially covered the wavelength spectrum of blue light, which are called cross talk problems. Despite being available to use such kinds of light intensity sensing devices for detecting light intensity, it is still possible to reduce the depth range and accuracy of optical intensity detection for each color lights. Therefore, the present invention further provides an alternative embodiment for reducing the cross talk problem by using independent color filter for separately filtering wavelength spectrum of each color light thereby obtaining separate RGB depth curves respectively having FWHM values for differential calculation. The alternative embodiment is explained below.

Figure 6A:
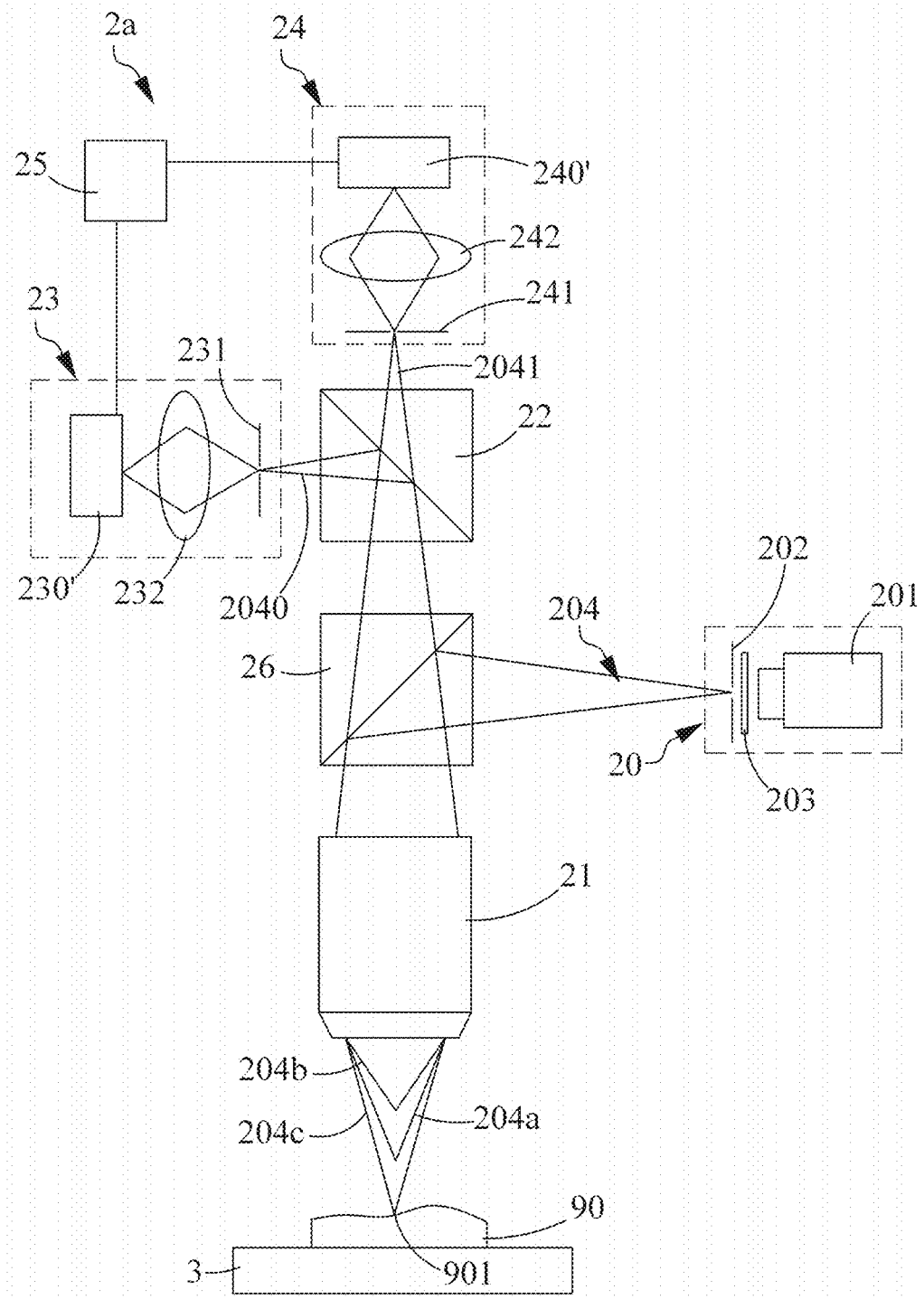
FIG. 6A illustrates a differential filtering chromatic confocal microscopic system according to a second embodiment of the present invention.

Please refer to FIG. 6A, which illustrates a differential filtering chromatic confocal microscopic system according to a second embodiment of the present invention. The confocal microscopic system 2a is basically similar to the system shown in FIG. 1, wherein the difference is that the light generated by the light source module 20 is a broadband light with a monochromatic spectrum such as red light spectrum 620 nm~750 nm, green light spectrum 495 nm~570 nm, or blue light spectrum 476 nm~495 nm, each of which could be the broadband light emitted from the light source module 20.

In one embodiment, the light source module 20 comprises a color filter 203 such as red light filter, green light filter, or blue light filter, which allows a monochromatic spectrum passing therethrough. The color filter 203 is arranged between the shaping element 202, and the light generating device 201. When the white light generated from the light generating device 201 passes the color filter 203, a monochromatic broadband light 204 that is allowed to pass the color filter 203 can be formed. The monochromatic broadband light 204 is further passes the chromatic dispersion objective 21 thereby further forming a plurality of dispersed lights 204a~204c which representatively show a continuous wavelength distribution of the monochromatic broadband light 204 passing through the color filter 203. The plurality of dispersed lights 204a~204c are projected onto an inspected position of the object 90 and are reflected therefrom to form an object light which is further divided into a first object light 2040 and a second object light 2041 by the first optical modulation module 22, which is a beam splitter in the present embodiment.

The first and second object lights 2040 and 2041 respectively pass through the spatial filters 231 and 241. The filtered first and second object lights 2040 and 2041 are sensed by the first light intensity sensing device 230' and 240' thereby generating a first and second optical intensity signals. It is noted that the first light intensity sensing device 230' and 240' can be a monochromatic CCD but it should not be limited thereto; for example, the color CCD can be used to detected the optical intensity of the first and second object lights as well.

The signal processing unit 25 receives the first and second optical intensity signals generated from the first light sensing units 230' and 240' and processes the first and second optical intensity signals by the normalization procedure and differential rational value calculation. In the present invention, the signal processing unit 25 possesses a relation between signal intensity ratio and object surface depth corresponding to a specific monochromatic spectrum, which could be the linear segment AB of red light, linear segment BC of green light, or linear segment CD of blue light shown in FIG. 5.

The signal processing unit 25 performs another signal processing on the first and second optical intensity signals according to Equation 1-7, 1-8, or 1-9 thereby obtaining differential rational value of optical intensity corresponding thereto. The differential rational values of optical intensity can be utilized to determine the depth of the inspected position 901 according to the relation between signal intensity ratio and object surface depth.

Figure 6B:
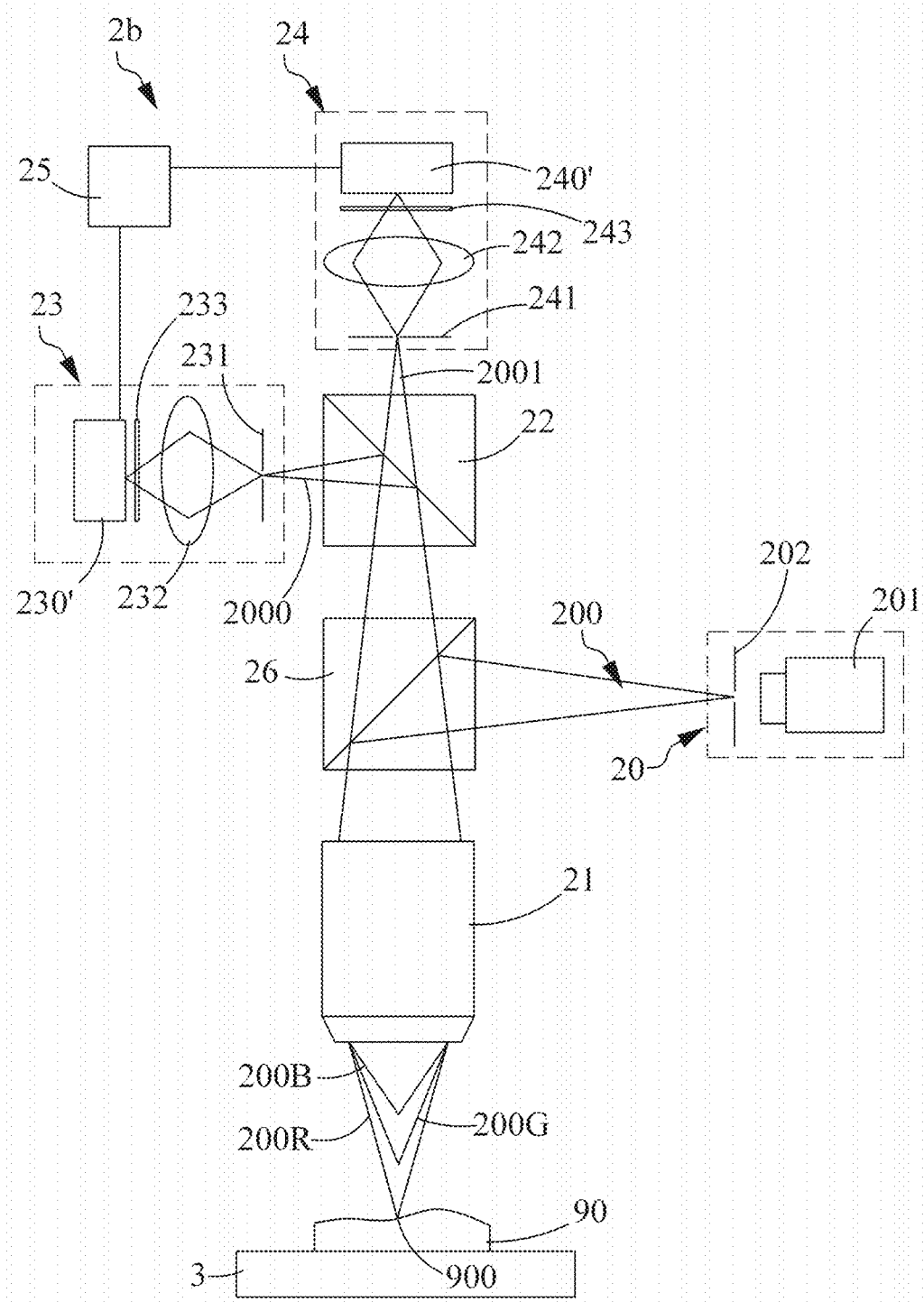
FIG. 6B illustrates a differential filtering chromatic confocal microscopic system according to a third embodiment of the present invention.
Figure 7:
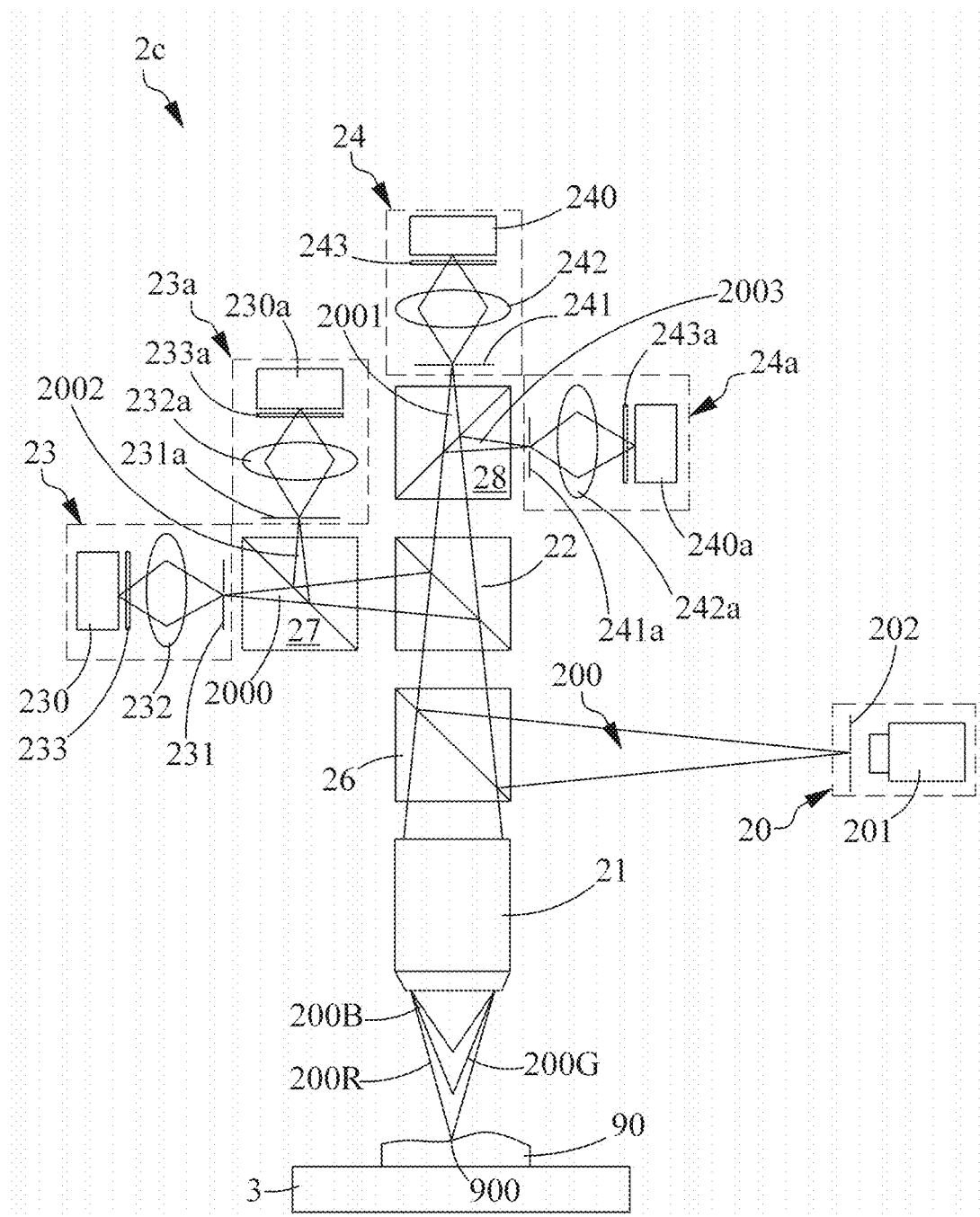
FIG. 7 illustrates a differential filtering chromatic confocal microscopic system according to a fourth embodiment of the present invention.

Please refer to FIG. 6B, which illustrates a differential filtering chromatic confocal microscopic system according to a third embodiment of the present invention. In the present invention, the system 2b is basically similar to the system shown in FIG. 1, wherein the difference therebetween is that the first optical intensity sensing module 23 and 24 respectively comprise a monochromatic color filters 233 and 243 which are respectively arranged between the first light intensity sensing devices 230' and 240' and collecting elements 232 and 242. The monochromatic color filters 233 and 243 respectively filter the first and second object lights 2000 and 2001 so as to form two monochromatic object lights, respectively, wherein one of the monochromatic object light is detected by the first light intensity sensing device 230' for generating a first optical intensity signal and the other monochromatic object light is detected by the second light intensity sensing device 240' for generating a second optical intensity signal. Like the embodiment shown in FIG. 6A, the first light sensing devices 230' and 240' can be a monochromatic CCD but should not be limited thereto. For example, color CCD can also be an alternative of the first light intensity sensing device. Regarding the signal processing of the signal processing unit 25, it is similar to the embodiment shown in FIG. 6A, which will not be further described hereinafter Please refer to FIG. 7, which illustrates a differential filtering chromatic confocal microscopic system according to a fourth embodiment of the present invention. Likewise, the present embodiment is similar to the system shown in FIG. 6B, wherein the difference is that there have two different kinds of color filters, each of which allows a specific range of wavelength spectrum to pass therethrough. In addition, the system 2c further comprises a second and a third optical modulation modules 27 and 28, wherein the second optical modulation module 27 is a beam splitter for forming a first sub object light 2002 split from the first object light 2000 while the third optical modulation module 28 is a beam splitter for forming a second sub object light 2003 split from the second object light 2001.

In addition to the first spatial filters 231 and 241, the collecting elements 232 and 242, and light intensity sensing devices 230 and 240, in the present embodiment, the first optical intensity sensing modules 23 and 24 respectively comprise a first color filters 233 and 243, wherein the first color filters 233 and 234 allows light having a first and a second color wavelength spectrum such as red and green light spectrum passing therethrough whereby the first and second object lights 2000 and 2001 passing through the first spatial filters 231 and 241 will further pass therethrough and will be filtered to form filtered first and second object lights, each of which has red light spectrum and green light spectrum. The red light spectrum and green light spectrum of the filtered first and second object lights are respectively detected by the light intensity sensing device 230 of optical intensity sensing module 23 and light intensity sensing device 240 of optical intensity sensing module 24 thereby generating a first and a second optical intensity signal, each of which, in the present embodiment, has red and green lights intensity signals.

Meanwhile, the second optical intensity sensing modules 23a and 24a are respectively utilized to detect the first and second sub object lights 2002 and 2003. Like the first optical intensity sensing modules 23 and 24, the second optical intensity sensing modules 23a and 24a respectively comprise second light intensity sensing devices 230a and 240a, second spatial filters 231a and 241a, and second spatial filters 233a and 243a, which are respectively arranged between the second light intensity sensing device 230a and 240a, and the second spatial filters 231a and 241a. In the present embodiment, the second color filter 233a allows green light and blue light spectrum of the first sub object light 2002 to pass therethrough while the second color filter 243a allows green light and blue light spectrum of the second sub object light 2003 to pass therethrough. In addition, the dimension of the second spatial filters 231a and 241a are different from each other. For example, if the second spatial filter 231a and 241a are slit structures, the dimension is referred to the width of the slit opening while if the second spatial filter 231a and 241a are pinhole structures, the dimension is referred to the diameter of the pinhole. In the present embodiment shown in FIG. 7, the second spatial filters 231a and 241a are the pinhole structures wherein the pinhole dimension of spatial filter 231 and 231a are corresponding to each other while the pinhole dimension of spatial filter 241 and 241a are corresponding to each other.

The second light intensity sensing device 230a detects the first sub object light 2002 passing through the second spatial filter 231a and the second color filter 233a thereby obtaining a third optical intensity signal corresponding to the inspected position 900 on the surface of the object; meanwhile, the second light intensity sensing device 240a detects the second sub object light 2003 passing through the second spatial filter 241a and the second color filter 243a thereby obtaining a fourth optical intensity signal. In the present embodiment, the third optical intensity signal and the fourth optical intensity signal are corresponding to the intensity of green and blue light spectrum.

The signal processing unit 25 performs a signal processing including, the intensity normalization procedure and differential calculation procedure, on the first and second optical intensity signals and the third and fourth optical intensity signals thereby obtaining a first differential rational value of optical intensity and a second differential rational value of optical intensity respectively corresponding to the first and second optical intensity signals, and the third and fourth optical intensity signals, wherein the first differential rational value of optical intensity comprises the differential rational values of red light intensity and green light intensity while the second differential rational value of optical intensity comprises the differential rational values of green light intensity and blue light intensity. Finally, the depth of the inspected position 900 on the surface of the object can be determined according the calculated first and second differential rational values and relation between signal intensity ratio and object surface depth, such as the curve shown in FIG. 3.

Figure 8:
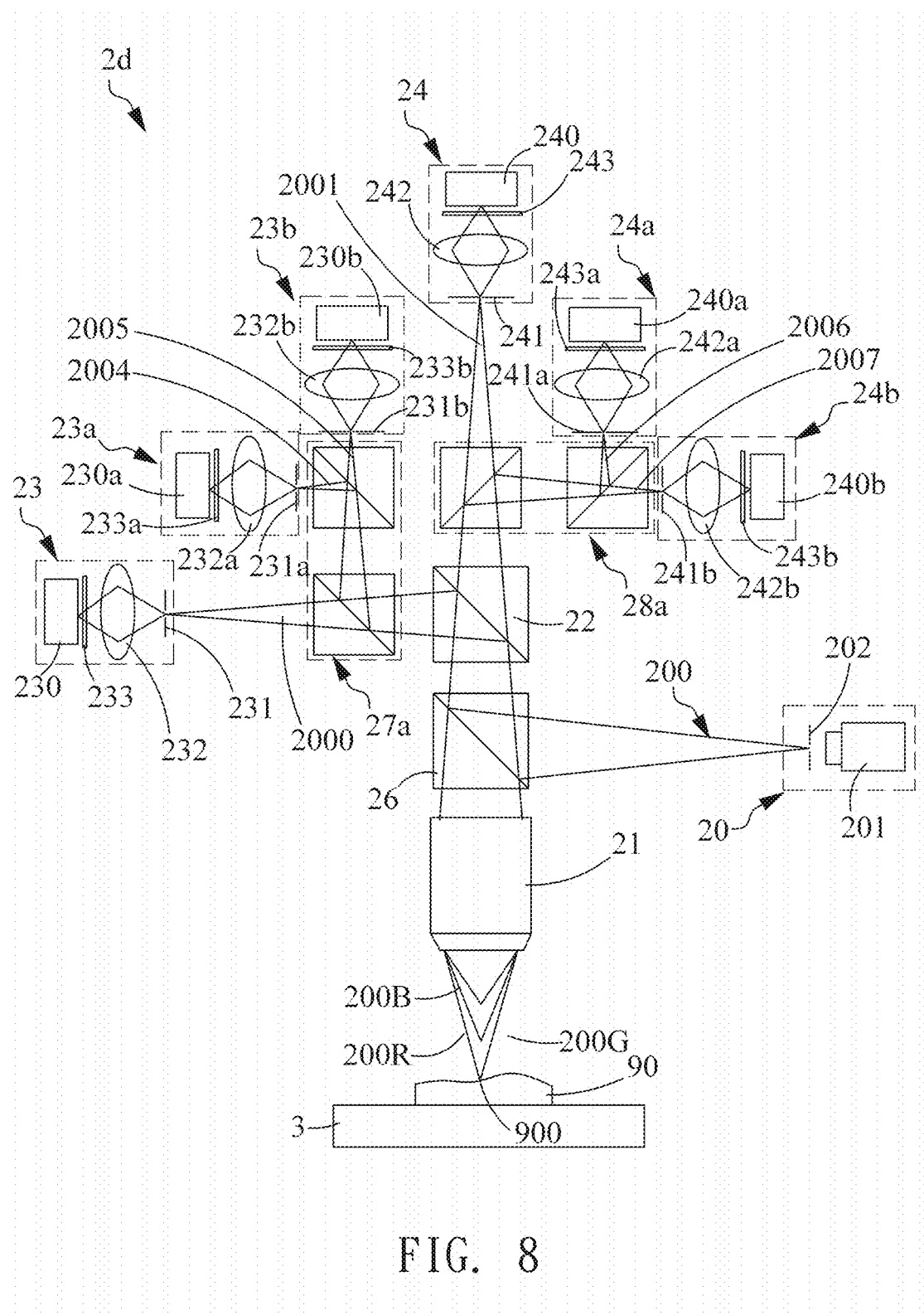
FIG. 8 illustrates a differential filtering chromatic confocal microscopic system according to a fifth embodiment of the present invention.

Please refer to FIG. 8, which illustrates a differential filtering chromatic confocal microscopic system according to a fifth embodiment of the present invention. In the present embodiment, similar to FIG. 7, the difference therebetween is that there have three sets of color filters allow different range of monochromatic wavelength spectrum passing therethrough, respectively. In the present embodiment, the three sets of color filters includes first color filters 233, 243 allowing a wavelength spectrum of red light passing therethrough, second color filters 233a, and 243a, allowing a wavelength spectrum of green light passing therethrough, and third color filters 233b, and 243b, allowing a wavelength spectrum of blue light passing therethrough. In the light source module 20, the light generating device 201 provides a white broadband light 200 and the shaping element 202 modulates the shape of the broadband light 200 into a point-shaped or linear-shaped broadband light. In the present invention, the shape of the white broadband light 200 is point-shaped broadband light.

Moreover, in the present embodiment, there has two optical modulation modules 27a and 28a wherein the optical modulation module 27a generates a first sub object light 2004 and second sub object light 2005 split from the first object light 2000 while the optical modulation module 28a generates a third sub object light 2006 and fourth sub object light 2007 split from the second object light 2001. The first and second object lights 2000 and 2001 are respectively detected by the pair of the first optical intensity sensing modules 23 and 24. In the present embodiment, the first optical intensity sensing modules 23 and 24 respectively has a first color filter 233 and 243 allowing red light spectrum passing through. The light intensity sensing device 230 detects the first object light 2000 sequentially passing through the first spatial filer 231, collecting element 232 and the first color filter 233 thereby obtaining a first optical intensity signal while the light intensity sensing device 240 detects the second object light 2001 sequentially passing through the first spatial filer 241, collecting element 242 and the first color filter 243 thereby obtaining a second optical intensity signal, wherein the first spatial filter 231 and 241 are respectively arranged at focal position of the first and second object lights 2000 and 2001, and the dimension such as pinhole diameter or slit opening width of first spatial filter 231 and 241 are different from each other. In the present embodiment, the first light intensity sensing device 230 and 240 are monochromatic CCD, the second spatial filters 231 and 241 are pinhole structures having different pinhole diameter, and the first and second optical intensity signals are red light intensity signals.

In addition, the system 2d further comprises a pair of second optical intensity sensing module 23a and 24a, and a pair of third optical intensity sensing module 23b and 24b. The pair of second optical intensity sensing module 23a and 24a are respectively utilized to detect the first and the third sub object lights 2004 and 2006 and respectively comprises a second light intensity sensing devices 230a and 240a, a second spatial filters 231a and 241a, and the second color filters 233a and 243a allowing a green light spectrum to pass therethrough, wherein the second color filter 233a is disposed between the second light intensity sensing device 230a and the second spatial filter 231a while the second color filter 243a is disposed between the second light intensity sensing device 240a and the second spatial filter 241a.

Moreover, it is noted that the dimension of the second spatial filters 231a and 241a are different from each other and the arrangement position of the second spatial filters 231a and 241a are respectively at the focal position of the first and third sub object lights 2004 and 2006. The second light intensity sensing device 230a detects the first sub object light 2004 passing through the second spatial filter 231a, collecting element 232a, and the second color filter 233a thereby obtaining a third optical intensity signal corresponding to an inspected position 900 on the object surface, while the second light intensity sensing device 240a detects the third sub object light 2006 passing through the second spatial filter 241a, collecting element 242a, and the second color filter 243a thereby obtaining a fourth optical intensity signal corresponding to the inspected position 900 on the object surface. In the present embodiment, the second light intensity sensing device 230a and 240a are monochromatic CCD, the second spatial filters 231a and 241a are pinhole structure having different pinhole diameter, and the third and fourth optical intensity signals are green light intensity signals.

The pair of third optical intensity sensing module 23b and 24b are respectively utilized to detect the second and the fourth sub object lights 2005 and 2007 and respectively comprises a third light intensity sensing device 230b and 240b, a third spatial filter 231b and 241b, and the third color filters 233b and 243b allowing a blue light spectrum passing therethrough, wherein the third color filter 233b is disposed between the third light intensity sensing device 230b and the third spatial filter 231b while the third color filter 243b is disposed between the third light intensity sensing device 240b and the third spatial filter 241b.

Moreover, it is noted that the dimension of the third spatial filters 231b and 241b are different from each other and the arrangement position of the third spatial filters 231b and 241b are respectively located at the focal position of the second and fourth sub object lights 2005 and 2007. The third light intensity sensing device 230b detects the second sub object light 2005 passing through the third spatial filter 231b, collecting element 232b, and the third color filter 233b thereby obtaining a fifth optical intensity signal corresponding to the inspected position 900 on the object surface, while the third light intensity sensing device 240b detects the fourth sub object light 2007 passing through the third spatial filter 241b, collecting element 242b, and the third color filter 243b thereby obtaining a sixth optical intensity signal corresponding to the inspected position 900 on the object surface. In the present embodiment, the third light intensity sensing device 230b and 240b are monochromatic CCD, the second spatial filters 231b and 241b are pinhole structures having different pinhole diameter, and the fifth and sixth optical intensity signals are blue light intensity signals.

The signal processing unit 25 performs a signal processing including normalization and differential calculation on the first and second optical intensity signals, the third and fourth optical intensity signals and the fifth and sixth optical intensity signals thereby obtaining a first differential rational value of optical intensity corresponding to the first and second optical intensity signal, a second differential rational value of optical intensity corresponding to the third and fourth optical intensity signal, and a third differential rational value of optical intensity corresponding to the fifth and sixth optical intensity signal. Finally, the signal processing unit 25 further determine the depth of the inspected position 900 on the object surface according to the relation between signal intensity ratio and object surface depth and the calculated first, second and third differential rational values of optical intensity.

Figure 9A:
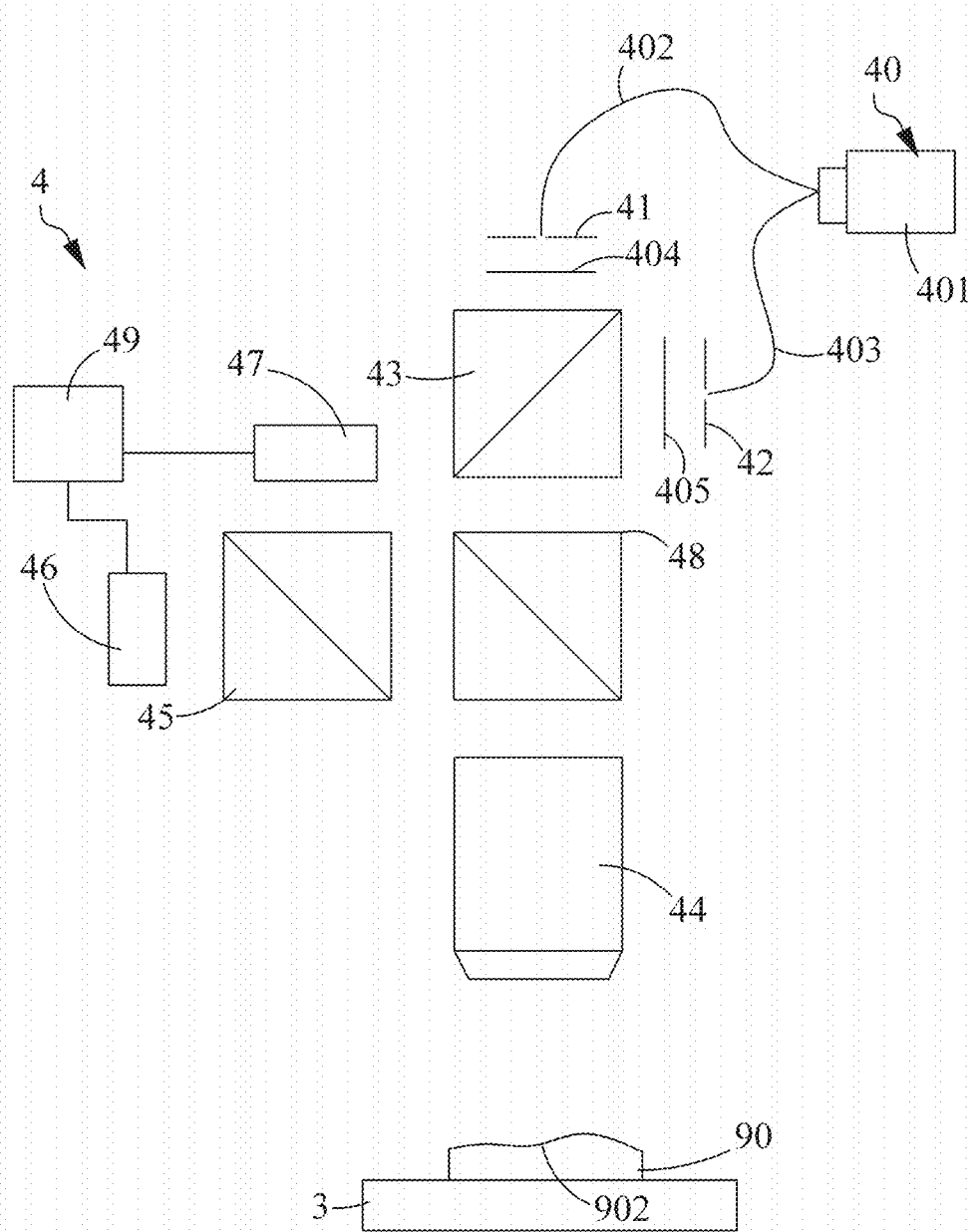
FIGS. 9A and 9B illustrate a differential filtering chromatic confocal microscopic system according to a sixth embodiment of the present invention.
Figure 9B:
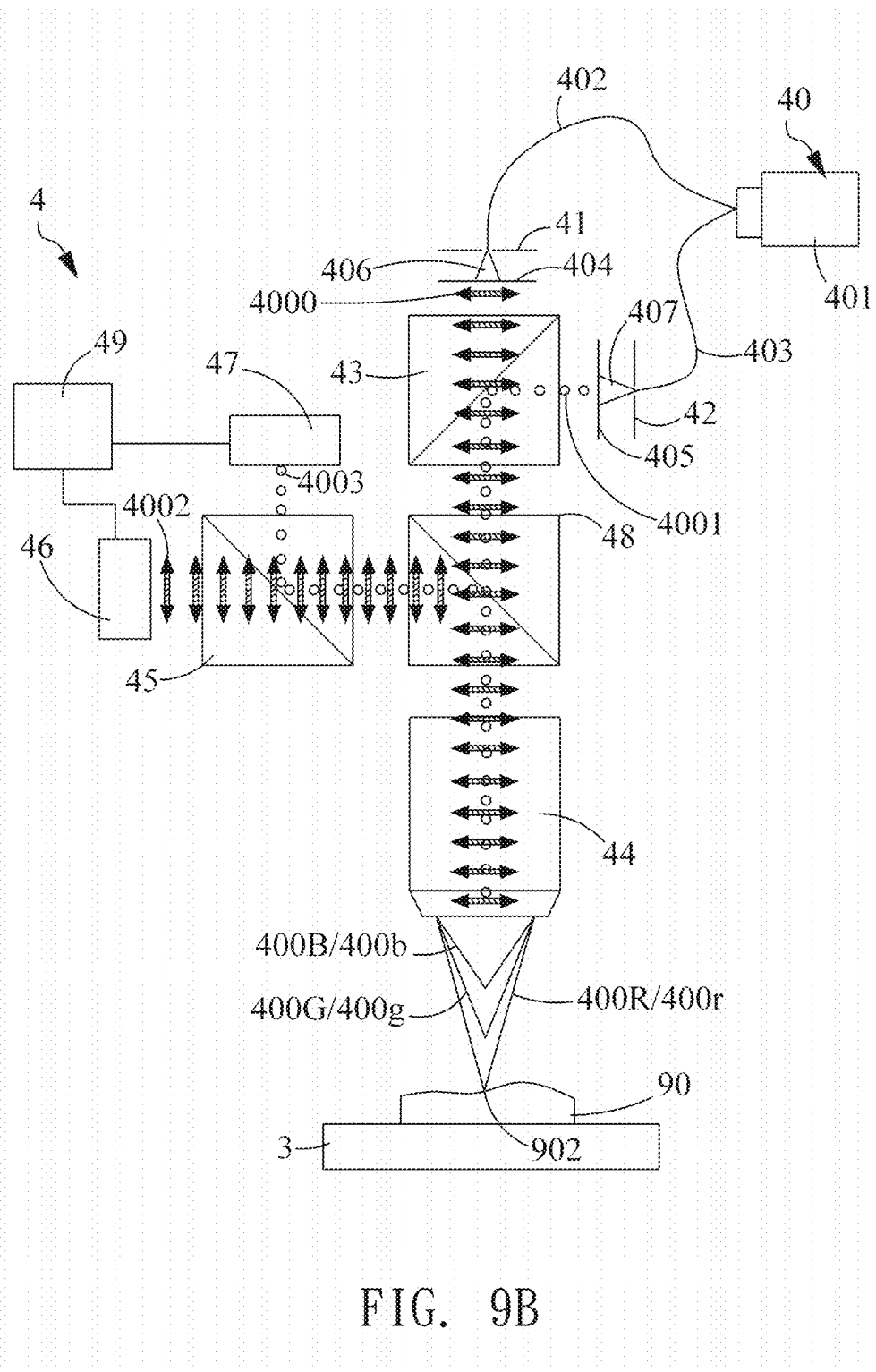

Please refer to FIGS. 9A and 9B, which illustrate a differential filtering chromatic confocal microscopic system according to a sixth embodiment of the present invention. In the present embodiment, the system 2e comprises a light source module 40, linear polarizing elements 404 and 405, spatial filters 41 and 42, a first optical modulation module 43, a chromatic dispersion objective 44, a second optical modulation module 45, optical intensity sensing modules 46 and 47, and a signal processing unit 49. The light source module 40 comprises a light generating device 401 for generating a broadband light, a pair of light guides 402 and 403 for dividing the broadband light into a first broadband light 406 and a second broadband light 407. The linear polarizing elements 404 and 405 respectively polarize the first and second broadband light 406 and 407 so as to form a first polarized broadband light (P polarized light) 4000, and a second polarized broadband light (S polarized light) 4001 orthogonal to the first polarized broadband light 4000. In the present embodiment, the broadband light is a white light, and the first and the pair of light guides 402 and 403 are made of optical fibers.

The first and the second spatial filters 41 and 42 respectively receive and filter the first and the second broadband lights 406 and 407. It is noted that the first and second spatial filters 41 and 42 has different dimension for spatially filtering the first and the second broadband lights, wherein the structure of the first and second spatial filters 41 and 42 can be slit structures or pinhole structures and the dimension corresponding to the slit structure refers to the slit opening while the dimension corresponding to the pinhole structure refers to the diameter of the pinhole. If the first and second spatial filters 41 and 42 are pinhole structures, the first and the second polarized broadband lights will be transformed into a point broadband light after passing through the first and the second spatial filters 41 and 42 while if the first and second spatial filters 41 and 42 are slit structures, the first and the second broadband lights will be transformed into a linear broadband light after passing through the first and the second spatial filters 41 and 42. In the present embodiment, the first and second spatial filters 41 and 42 are pinhole structures with diameter different from each other so as to modulate the first and second broadband lights into a point broadband lights projecting to the first optical modulation module 43.

The first optical modulation module 43 is a polarizing beam splitting element for receiving the first and second polarized broadband lights 4000 and 4001 and combined them together. The combined the first and second polarized broadband lights 4000 and 4001 are guided by a beam splitter 48 and enter the chromatic dispersion objective 44. It is noted that since the first and second polarized lights 4000 and 4001 are orthogonal to each other, the first and second polarized lights 4000 and 4001 will not interfere with each other even if they are combined as one after passing the first optical modulation module 43.

The chromatic dispersion objective 44 axially dispersed the first and second polarized broadband light 4000 and 4001 thereby forming a plurality of first sub polarized lights 400R, 400G, and 400B, as well as a plurality of second sub polarized lights 400r, 400g, and 400b. The plurality of first and second sub polarized lights 400R/r, 400G/g, and 400B/b project onto an inspected position 902 on the surface of the object 90 thereby reflecting to form a first polarized object light and a second polarized object light having the same optical path as each other. The first and second polarized object lights are guided by the beam splitter 48 and enter the second optical modulation module 45, which is a polarized beam splitter for splitting the first and second polarized object lights having the same optical path into the first and second polarized object lights, notated as 4002 and 4003, having different optical path from each other. In the present embodiment, the first polarized object light 4002 is orthogonal to the second polarized object light 4003.

The pair of optical intensity sensing modules 46 and 47 are color CCD, respectively, wherein one of the optical intensity sensing module 46 detects the first polarized object light 4002 thereby obtaining a first optical intensity signal corresponding to the inspected position 902 while the other optical intensity sensing module 47 detects the second polarized object light 4003 thereby obtaining a second optical intensity signal corresponding to the first optical intensity signal. In the present embodiment, the first optical intensity signal comprises a first red light intensity value, a first green light intensity value, and a first blue light intensity value while the second optical intensity signal comprises a second red light intensity value, a second green light intensity value, and a second blue light intensity value.

The signal processing unit 49 has a relation between the signal intensity ratio and object surface depth, such as the curve illustrated as FIG. 3. The signal processing unit 49 performs a signal process including normalization process and differential calculation process onto the first and second red light intensity values, the first and second green light intensity values and the first and second blue light intensity values thereby generating a first and second optical differential rational values of optical intensity which respectively comprise a red light differential intensity rational value differentially calculated from the first and second red light intensity values, a green light differential intensity rational value differentially calculated from the first and second green light intensity values and a blue light differential intensity rational value differentially calculated from the first and second blue light intensity values. It is noted that the differential rational value of optical intensity of each color light is calculated according to Equations 1-7~1-9, which are described in detail before and will not be described hereinafter. After calculating differential rational value of optical intensity of each color light, the signal processing unit 49 can determine depth of the inspected position 902 of the object surface according to the relation between signal intensity ratio and object surface depth.

In the embodiment shown in FIGS. 9A and 9B, since the wavelength spectrum emitted from the light generating device 401 is continuous, for example, wavelength ranging from 400 nm to 700 nm, the problem that the object under inspection may absorb a specific wavelength when light is projected onto the surface can be avoid. In addition, in order to increase the efficiency of light utilization without loss in the FIGS. 9A and 9B, the optical fibers 402 and 403 are utilized to be a light guide for guiding the broadband light emitted from the light generating device 401 into the optical system. The guided broadband lights are transformed into a point-shaped broadband light after being filtered by the pinhole spatial filters 41 and 42. After passing through the spatial filters 41 and 42, and polarizing elements 404 and 405, a P polarized light and S polarized light having the same optical path and orthogonal to each other are formed to project onto the first optical modulation module 43. The first optical modulation module 43 guided the P and S polarized lights to the chromatic dispersion objective 44 whereby the P and S polarized linear lights are axially dispersed and are projected onto the surface of object. The object lights reflected from the object surface pass through the beam splitter whereby the P and S polarized linear lights are split and are respectively detected by the pair of optical intensity sensing modules 46 and 47 arranged at the focal position of the P and S polarized object lights. In one embodiment, each one of optical intensity sensing modules 46 and 47 has triple CCDs for detecting R, G and B lights, respectively whereby each color light can be detected by independently corresponding CCD so as to prevent the cross talk occurred between the color lights.

Figure 10B:
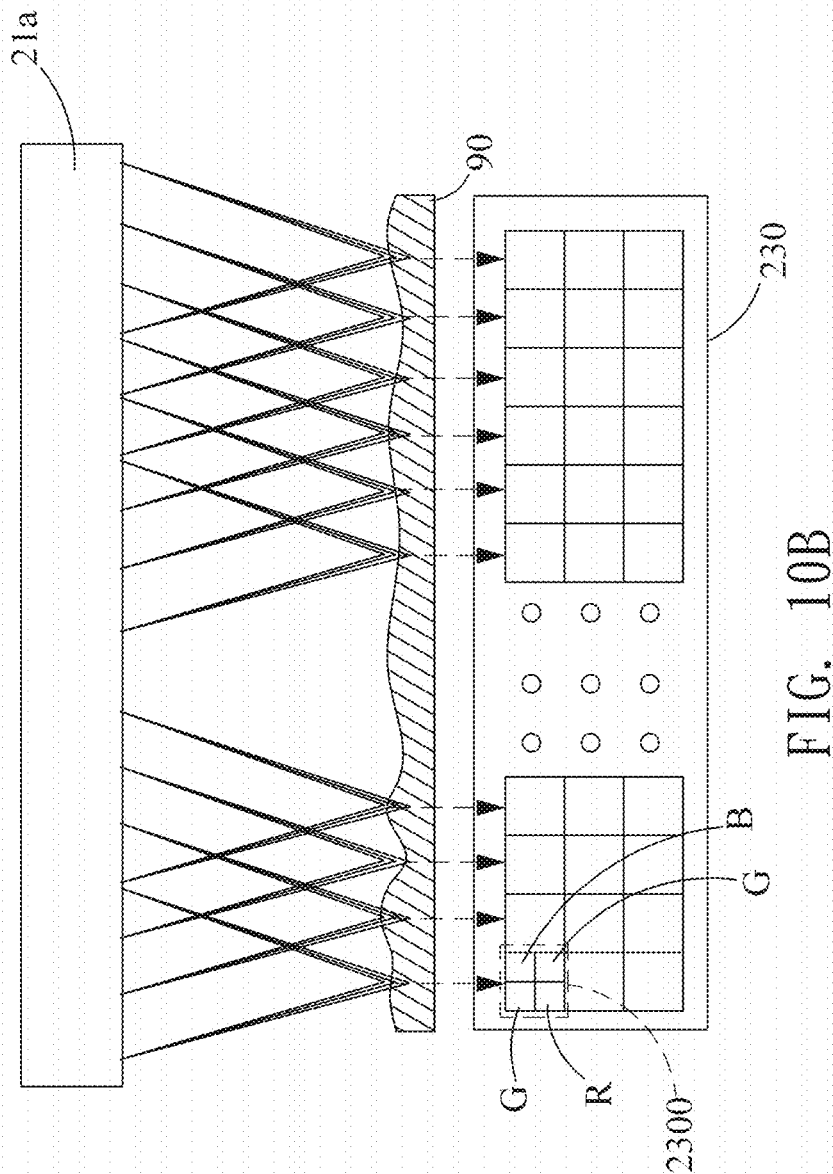

It is noted that although the broadband light in foregoing embodiments are referred to point broadband light, if the shaping element 202 or the spatial filters 41 and 42 are the slit structures, the broadband light emitted from the light generating device can be modulated into a linear broadband light. Taking the system 2 shown in FIG. 1 as an example, while the broadband light is a linear broadband light, it will be dispersed after passing through the chromatic dispersion objective 21 thereby forming a plurality of sub linear lights 200R(L), 200G(L), and 200B(L) projecting onto the surface of the object 90 as illustrated in FIG. 10A. Please refer to FIG. 10B, the reflected linear object light carried a one-dimensional surface profile corresponding to the projecting area are divided into first and second linear object lights respectively modulated by the corresponding spatial filter. The filtered first and second object lights are respectively detected by the light intensity sensing devices 230 and 240. Taking light intensity sensing device 230 detecting the first linear object light as an example, the light intensity sensing device 230 comprises a plurality of sensing pixels 2300, each of which has a plurality of sensing elements corresponding to RGB colors for generating a plurality of optical intensity signals after receiving the first linear object light entering the light intensity sensing device 230. According to the foregoing algorithm, the optical intensity signals generated from the light intensity sensing devices 230 and 240 are utilized to calculate the differential rational values of optical intensity. Since the linear broadband light projected onto the object surface can measured one-dimensional surface profile of the object, a two-dimensional surface profile of the object surface can be measured by moving the platform support the object thereby increasing the efficiency of the measurement.

First Inspection Example: Gauge Block

Figure 11A:
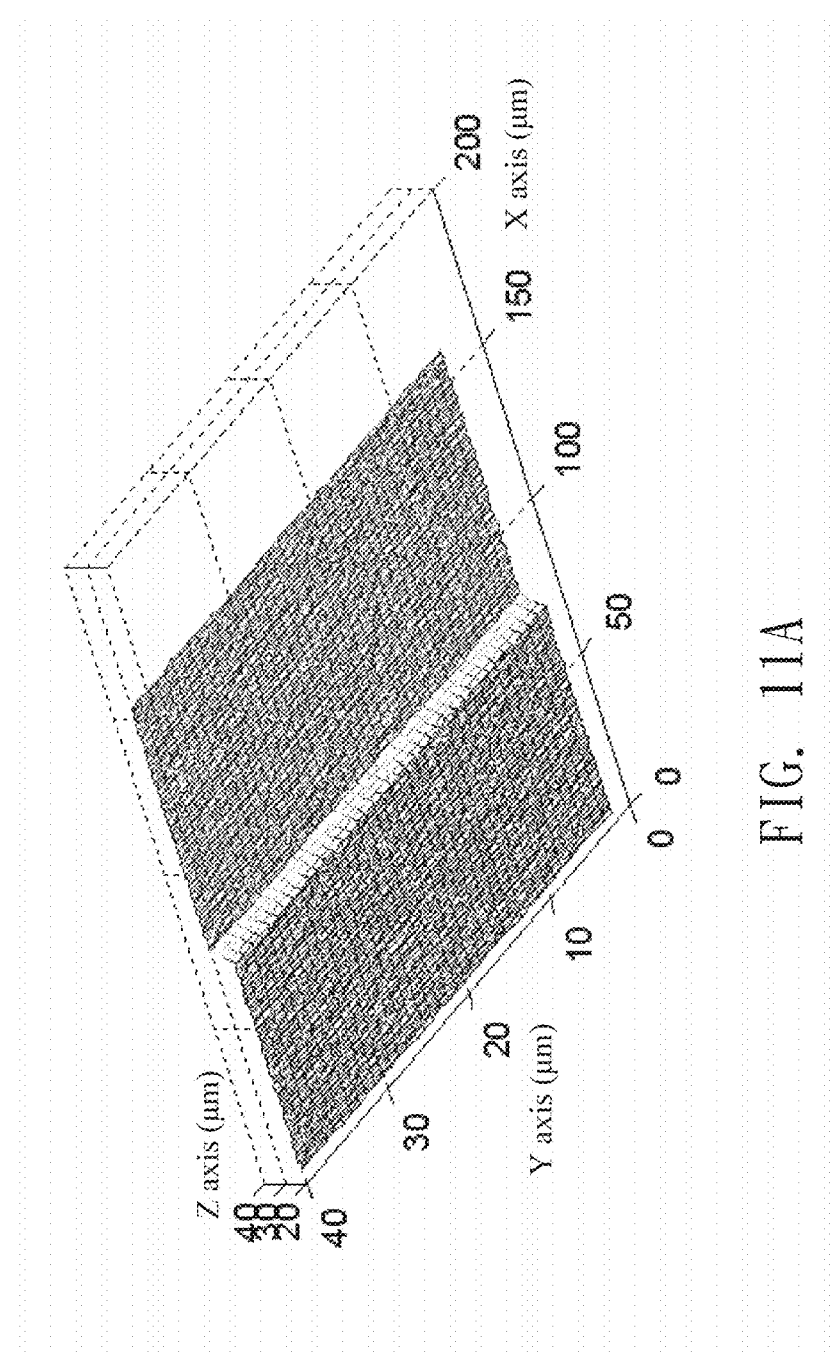
FIGS. 11A to 11D illustrate a surface profile and cross-section view of standard gauge block according to a measuring result of the present invention.
Figure 11B:
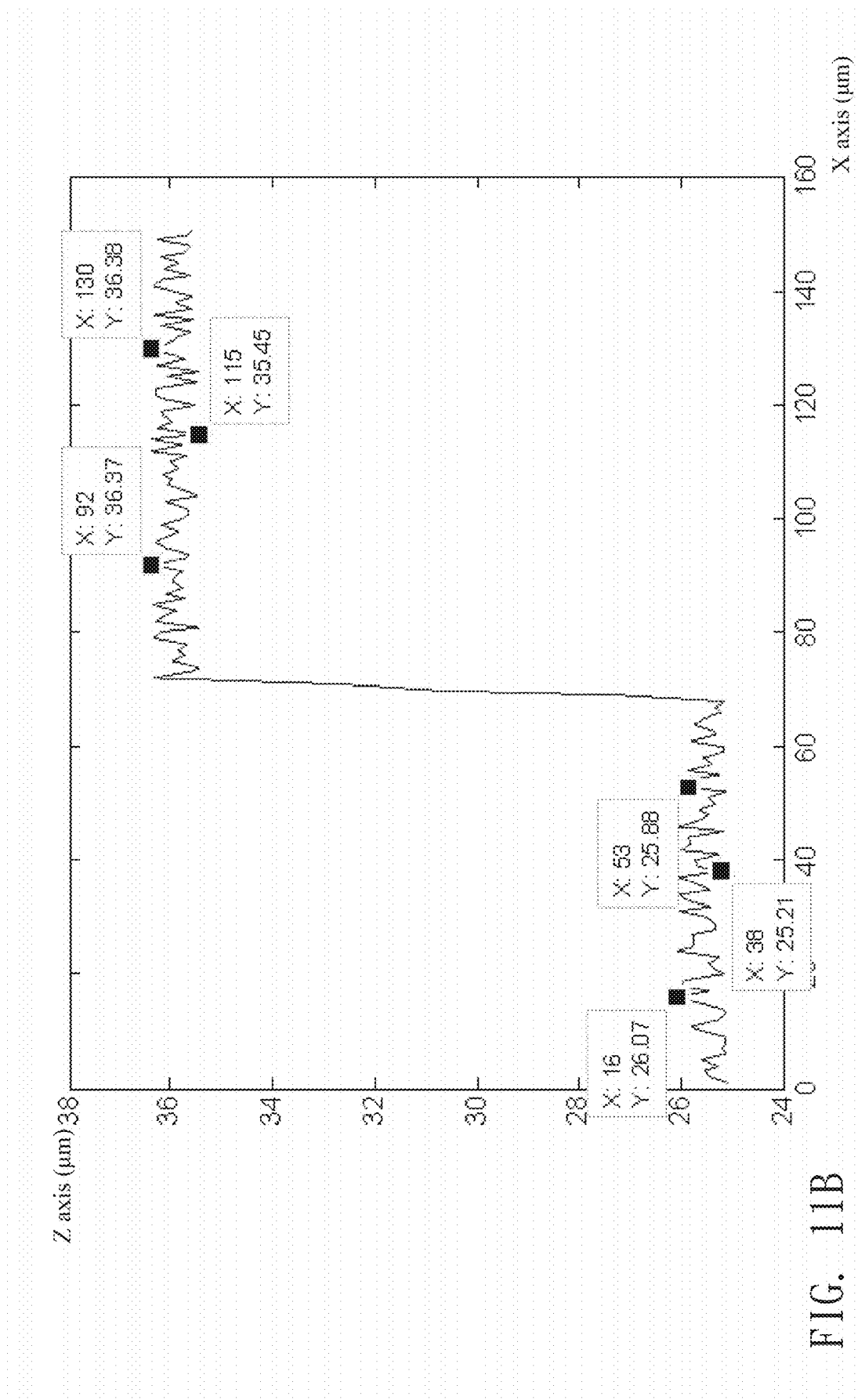

The first example is presented by measuring the surface profile of the gauge block having uniform surface depth 10.1 μm through the differential filtering chromatic confocal microscopic system of the present invention. The platform for supporting the gauge block can performs two-axial translation with 150×40 μm² scanning range and 0.5 μm scanning pitch. The measurement consequence is illustrated as FIGS. 11A and 11B, wherein the FIG. 11A refers to the 3D construction image according to the measuring result while the FIG. 11B refers to the cross-sectional profile of the gauge block surface. The average measured depth and standard derivative is shown in table 1 listed below.

TABLE 1

| average height (μm) | standard derivative (μm) |
|---|---|
| 9.792 | 0.111 |

Second Inspection Example: Gauge Block

Figure 11C:
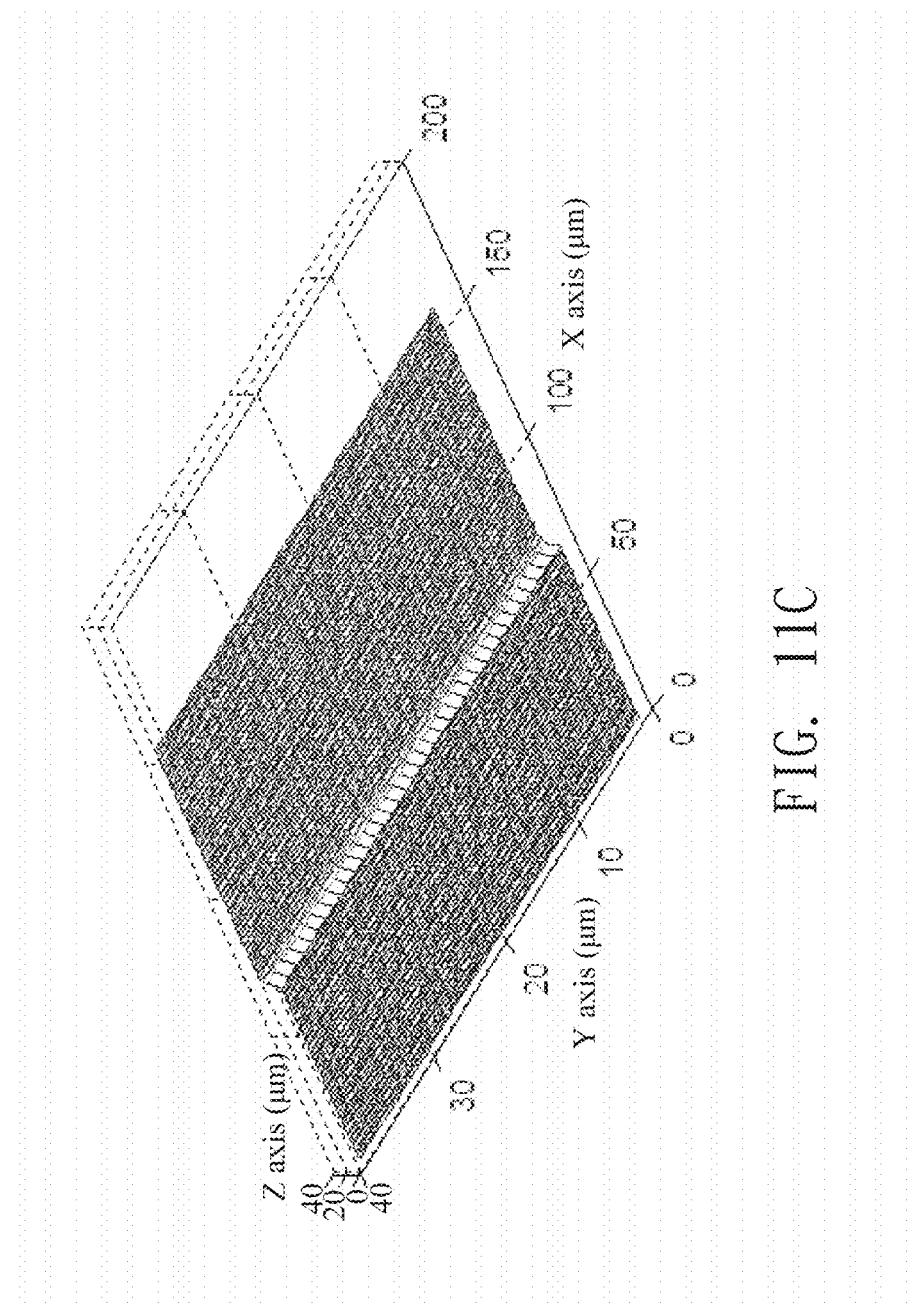
Figure 11D:
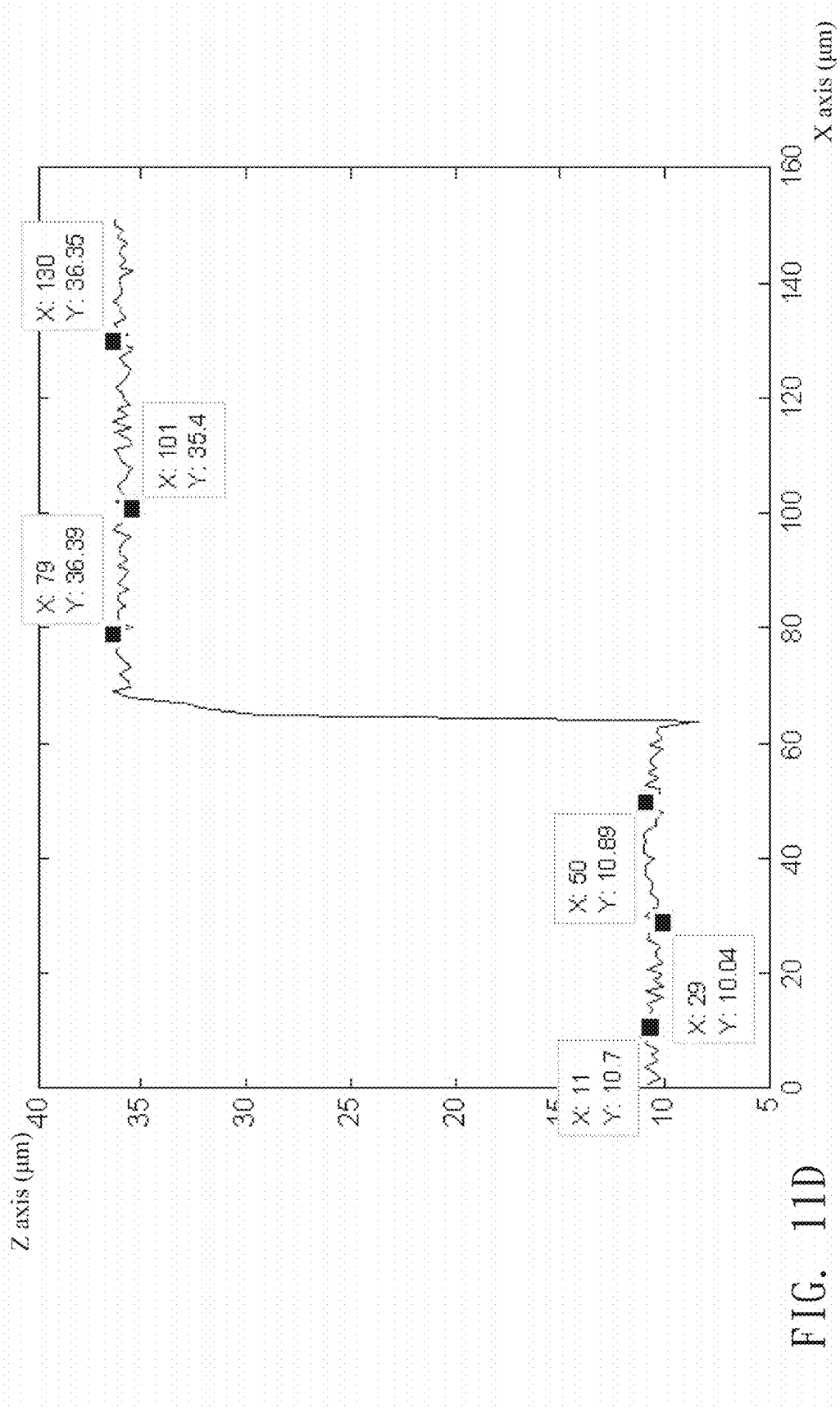

The second example is presented by measuring the surface profile of the gauge block having uniform surface depth 25.4 μm through the differential filtering chromatic confocal microscopic system of the present invention. The platform for supporting the gauge block can performs two-axial translation with 150×40 μm² scanning range and 0.5 μm scanning pitch. The measurement consequence is illustrated as FIGS. 11C and 11D, wherein the FIG. 11C refers to the 3D construction image according to the measuring result while the FIG. 11D refers to the cross-sectional profile of the gauge block surface. The average measured depth and standard derivative is shown in table 2 listed below.

TABLE 2

| average height (μm) | standard derivative (μm) |
|---|---|
| 25.187 | 0.108 |

Third Inspection Example: Micro Bump

Figure 12:
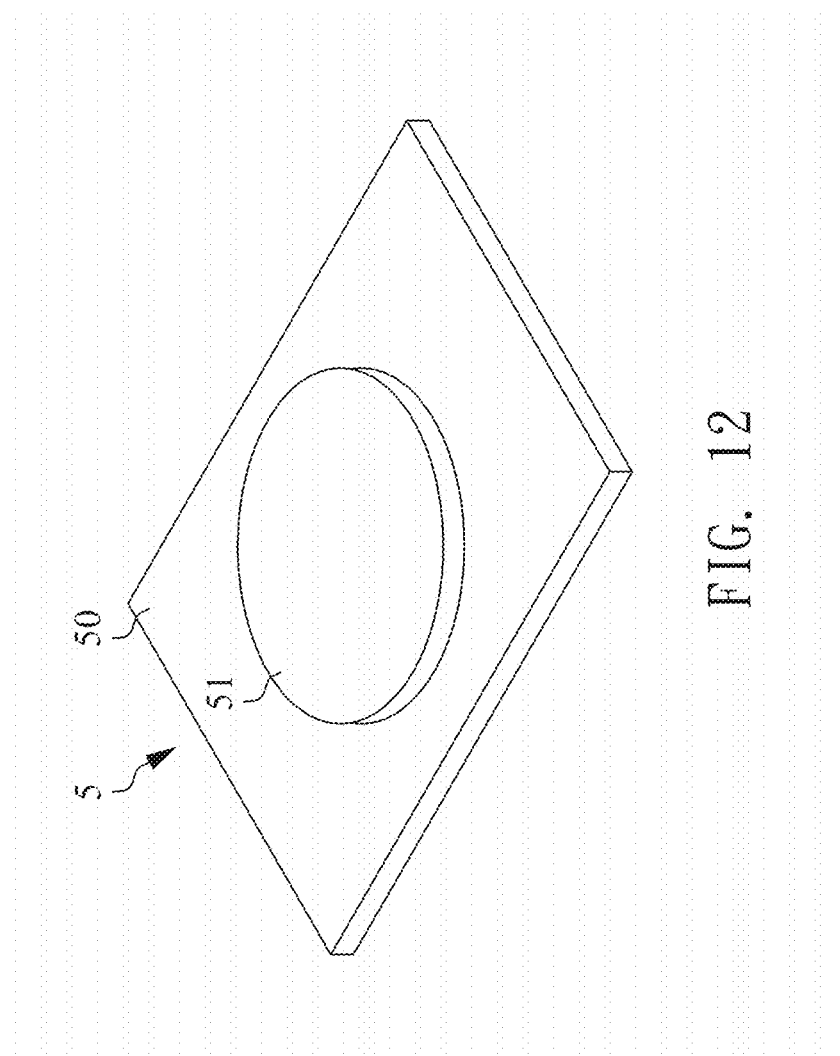
FIG. 12 illustrates a perspective view of a protrusion block of a circuit board.
Figure 13A:
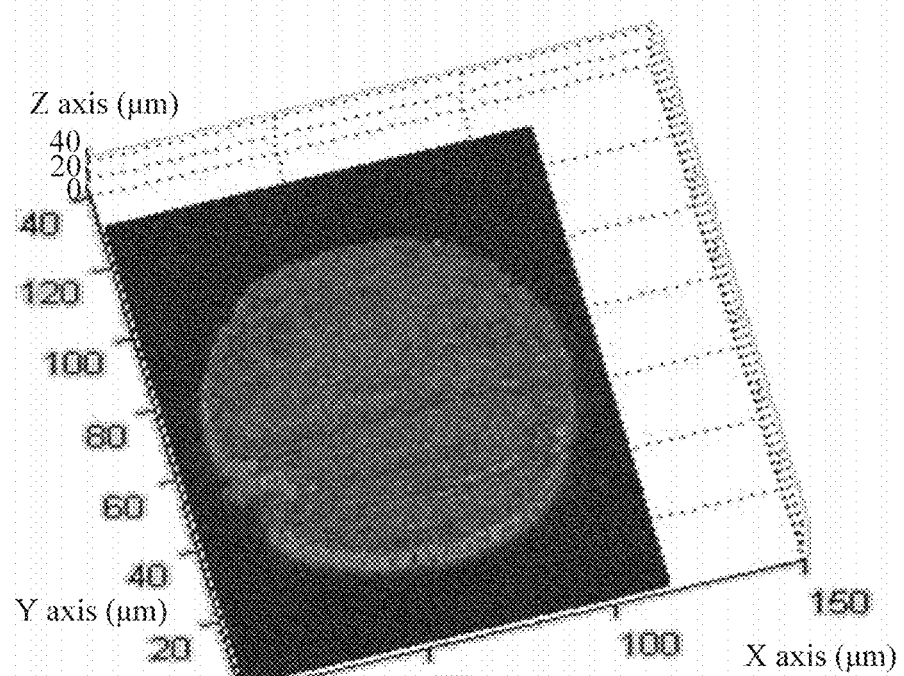
FIGS. 13A to 13C illustrate a surface profile and cross-section view of the protrusion block of circuit board according to a measuring result of the present invention.
Figure 13B:
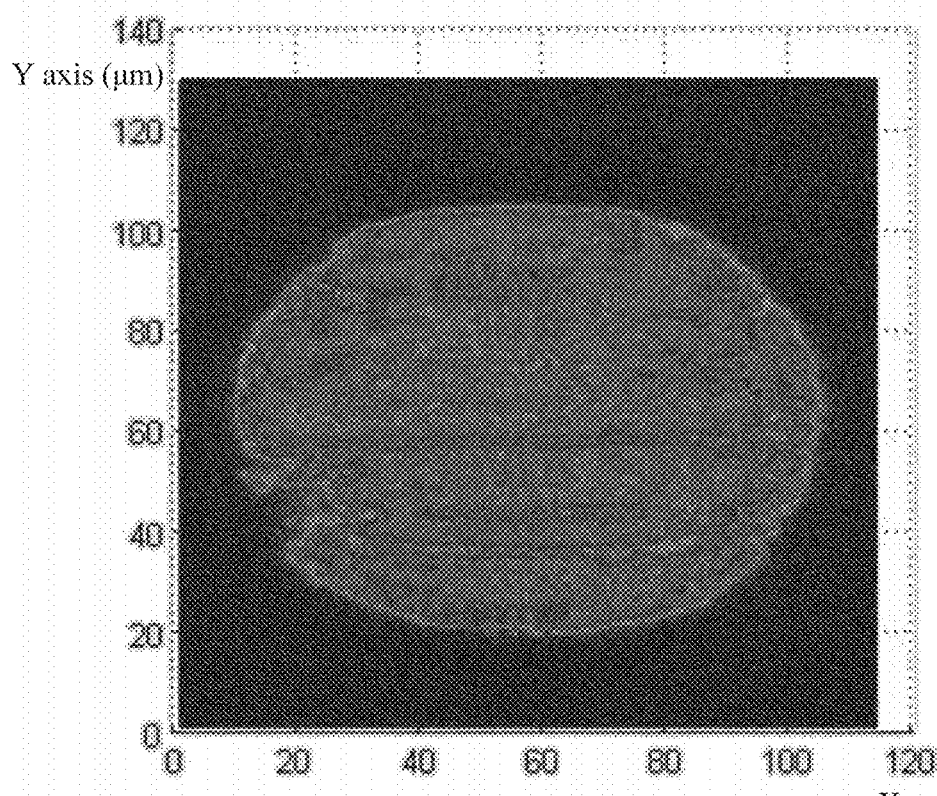
Figure 13C:
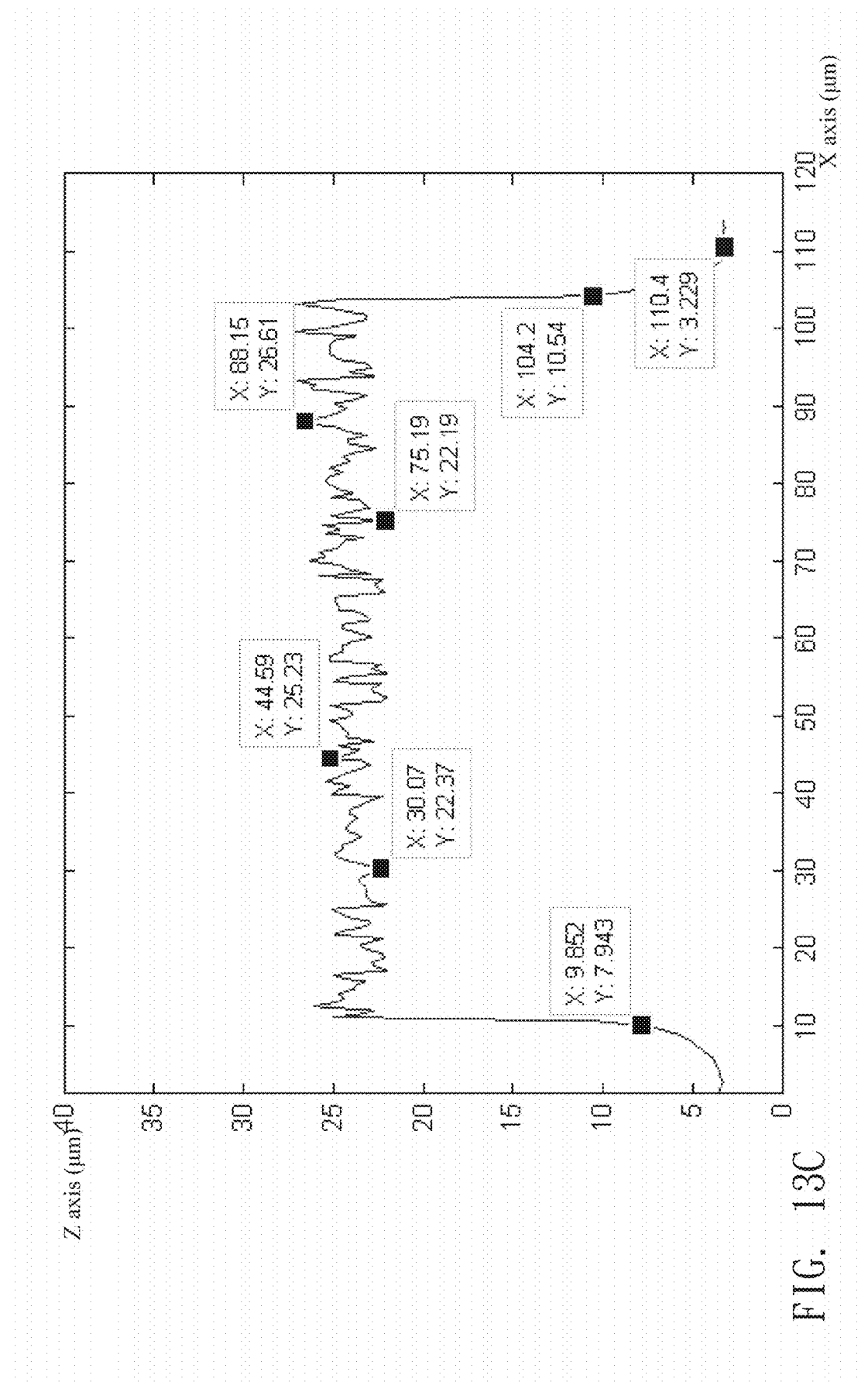

The micro bumps formed on a print circuit board (PCB) for industrial usage is taken as the third example for showing that the present invention has capability to be completely adapted in inspection industry. Please refer to FIG. 12, which illustrates PCB board and a micro bump formed thereon, wherein the PCB 5 has a substrate 50 and micro bump 51 which is formed by a metal material that can reflect white light spectrum. The reflecting rate of the surface of the micro bump 51 is different from the reflecting rate of the surface of substrate 50. Since each micro bump 51 may have different volume during the manufacturing process, the diameter and surface height can be inspected for calculating the volume of micro bump 51 so as to determine the quality of micro bump 51. The measurement consequence is illustrated as FIGS. 13A and 13B, wherein the FIG. 13A refers to the 3D construction image of micro bump according to the measuring result while the FIG. 13B refers to the cross-sectional profile of the surface of micro bump 51. The average measured depth and standard derivative is shown in table 3 listed below.

TABLE 3

| average height (μm) | standard derivative (μm) |
|---|---|
| 22.551 | 94.337 |

There has thus shown and described a novel differential filtering chromatic confocal microscopic system. Many changes, modifications, variations and other uses and application of the subject invention will become apparent to those skilled in the art after considering this specification and the accompanying drawings. All such changes, modifications, variations, uses, and applications are covered by the scope of this invention which is limited only by the appended claims.

What is claimed is:

1. A differential filtering chromatic confocal microscopic system, comprising:
a light source module, providing a broadband light;
a chromatic dispersion objective, axially dispersing the broadband light for forming a plurality of dispersed lights projecting onto an inspected location of an object and reflecting therefrom for forming an object light, wherein the plurality dispersed lights are co-axial and each respectively has a specific focal depth different from each other;
a first optical modulation module, splitting the object light into a first object light and a second object light, both of which are with respect to the inspected location on the object;
a first optical intensity sensing module, having a pair of first light intensity sensing devices and a pair of first spatial filters having different dimension from each other, wherein one of the first spatial filter is arranged at a focal position of the first object light whereby the first object light passing therethrough is detected by the corresponding first light intensity sensing device thereby obtaining at least one first optical intensity signal while the other first spatial filter is arranged at a focal position of the second object light whereby the second object light passing therethrough is detected by the corresponding second light intensity sensing device thereby obtaining at least one second optical intensity signal, wherein the pair of first spatial filters are respectively a slit structure and the different dimension is referred to the pair of the first spatial filters having a different opening width of the slit structure, or the pair of first spatial filters are respectively a pinhole and the different dimension is referred to the pair of the first spatial filters having a different diameter of the pinhole; and
a signal processing unit, determining depth of at least one measured depth information on the inspected location of the object according to the corresponding at least one first optical intensity signal and at least one second optical intensity signal.

2. The system of claim 1, wherein the broadband light is a visible light with a spectrum formed by a plurality of color lights and the pair of the first light intensity sensing devices are color sensing devices wherein one of the first light intensity sensing devices detects the first object light for obtaining the at least one first optical intensity signal comprising a first red light intensity signal, a first green light intensity signal, and a first blue light intensity signal and the other first light intensity sensing device detects the second object light for obtaining the at least one second optical intensity signal comprising a second red light intensity signal, a second green light intensity signal, and a second blue light intensity signal.

3. The system of claim 1, wherein the broadband light is a visible light with a spectrum formed by single color light and the pair of the first light intensity sensing devices are color or monochrome sensing devices wherein one of the first light intensity sensing devices detects the first object light for obtaining the at least one first optical intensity signal corresponding to the single color light and the other first light intensity sensing device detects the second object light for obtaining the at least one second optical intensity signal corresponding to the single color light.

4. The system of claim 1, wherein the signal processing unit further comprises a relation between signal intensity ratio and object surface depth and executes a process on each first optical intensity signal and the corresponding second optical intensity signal thereby obtaining a first differential rational value of optical intensity, and determines the depth of each inspected position of the object according to the first differential rational value of optical intensity and the relation between signal intensity ratio and object surface depth.

5. The system of claim 4, wherein the broadband light is a visible light with a spectrum formed by a plurality of color lights and the pair of the first light intensity sensing devices are monochrome sensing devices wherein a first color filter allowing at least one wavelength or color spectrum passing therethrough is disposed between each first light intensity sensing device and the corresponding first spatial filter whereby the pair of the first light intensity sensing devices respectively detect the first and second object lights passing through the first spatial filter and the first color filter, thereby obtaining the first optical intensity signal and the second optical intensity signal.

6. The system of claim 5, wherein the first color filter allows a first and a second optical wavelengths or color spectrums passing therethrough, and the system further comprises:
a second optical modulation module, splitting a first sub object light from the first object light;
a third optical modulation module, splitting a second sub object light from the second object light;
a second optical intensity sensing module, comprising a pair of second light intensity sensing devices, a pair of second spatial filters having different dimension from each other and being respectively arranged at a focal position of the first and the second sub object lights, each second spatial filter being corresponding to one of the second light intensity sensing device, and a pair of second color filters, each of which is disposed between the corresponding second light intensity sensing device and second spatial filter and allows the second and a third optical wavelengths or color spectrums passing therethrough, wherein one of the second light intensity sensing devices detects the first sub object light passing through the corresponding second spatial filter and the second color filter thereby generating at least one third optical intensity signal while the other one of the second light intensity sensing devices detects the second sub object light passing through the corresponding second spatial filter and the second color filter, thereby generating at least one fourth optical intensity signal respectively associates with the at least one third optical intensity signal wherein the pair of second spatial filters are respectively a slit structure and the different dimension is referred to the pair of the second spatial filters having a different opening width of the slit structure, or the pair of second spatial filters are respectively a pinhole and the different dimension is referred to the pair of the second spatial filters having a different diameter of the pinhole;

wherein the signal processing unit performs the process on each third optical intensity signal and the corresponding fourth optical intensity signal, thereby obtaining a second differential rational value of optical intensity, and determines the depth of each inspected position of the object according to the first and the second differential rational values of optical intensity and the relation between signal intensity ratio and object surface depth.

7. The system of claim 6, wherein the second spatial filter is a slit structure whose dimension is referred to an opening width of the slit structure, or the second spatial filter is a pinhole whose dimension is referred to a diameter of the pinhole.

8. The system of claim 5, wherein the first color filter allows a first optical wavelength or color spectrum passing therethrough, and the system further comprises:
a second optical modulation module, splitting a first and a second sub object lights from the first object light;
a third optical modulation module, splitting a third and a fourth sub object lights from the second object light;
a second optical intensity sensing module, comprising a pair of second light intensity sensing devices, a pair of second spatial filters having different dimension from each other and being respectively arranged at a focal position of the first and second sub object lights, each second spatial filter being corresponding to one of the second light intensity sensing device, and a pair of second color filters, each of which is disposed between the corresponding second light intensity sensing device and second spatial filter and allows a second optical wavelength or color spectrum passing therethrough, wherein one of the second light intensity sensing devices detects the first sub object light passing through the corresponding second spatial filter and the second color filter thereby generating at least one third optical intensity signal while the other one of the second light intensity sensing devices detect the second sub object light passing through the corresponding second spatial filter and the second color filter thereby generating at least one fourth optical intensity signal respectively associated with the at least one third optical intensity signal; and a third optical intensity sensing module, comprising a pair of third light intensity sensing devices, a pair of third spatial filters having different dimension from each other and being respectively arranged at a focal position of the third and fourth sub object lights, each third spatial filter being corresponding to one of the third light intensity sensing device, and a pair of third color filters, each of which is disposed between the corresponding third light intensity sensing device and third spatial filter and allows a third optical wavelength or color spectrum passing therethrough, wherein one of the third light intensity sensing devices detects the third sub object light passing through the corresponding third spatial filter and the third color filter thereby generating at least one fifth optical intensity signal while the other one of the third light intensity sensing devices detects the fourth sub object light passing through the corresponding third spatial filter and the third color filter thereby generating at least one fourth optical intensity signal respectively associated with the at least one sixth optical intensity signal;

wherein the signal processing unit performs the process on each third optical intensity signal and the corresponding fourth optical intensity signal thereby obtaining a second differential rational value of optical intensity, and on each fifth optical intensity signal and the corresponding sixth optical intensity signal thereby obtaining a third differential rational value of optical intensity, and determines the depth of each inspected position of the object according to the first, the second and the third differential rational values of optical intensity and the relation between signal intensity ratio and object surface depth.

9. The system of claim 8, wherein the third spatial filter is a slit structure whose dimension is referred to an opening width of the slit structure, or the third spatial filter is a pinhole whose dimension is referred to a diameter of the pinhole.

10. The system of claim 1, wherein the broadband light is a point broadband light or a linear broadband light.

11. The system of claim 1, wherein the first and the second light intensity signal respectively comprises at least one color intensity signal and the signal processing unit further includes a normalization procedure for modulating magnitude of each color intensity signal within a range between 0 and 1.

12. The system of claim 11, wherein the differential rational value of optical intensity is calculated by dividing a difference of optical intensity detected by the pair of the first light intensity sensing devices to a summation between optical intensity detected by the pair of the first light intensity sensing devices.

* * * * *

UNITED STATES PATENT AND TRADEMARK OFFICE
CERTIFICATE OF CORRECTION

PATENT NO. : 10,082,655 B2  
APPLICATION NO. : 14/464061  
DATED : September 25, 2018  
INVENTOR(S) : Liang-Chia Chen and Jiun-Da Lin Page 1 of 1

It is certified that error appears in the above-identified patent and that said Letters Patent is hereby corrected as shown below:

On the Title Page

Item (30) Foreign Application Priority Data should be as the following:
(30) Foreign Priority Application Priority Data
Aug. 20, 2013 (TW) 102129816

Signed and Sealed this
Sixteenth Day of June, 2020

Andrei Iancu
*Director of the United States Patent and Trademark Office*